United States Patent [19]
Cohen

[11] Patent Number: 4,967,748
[45] Date of Patent: Nov. 6, 1990

[54] O₂ LEVEL RESPONSIVE SYSTEM FOR AND METHOD OF TREATING A MALFUNCTIONING HEART

[75] Inventor: Todd J. Cohen, Mountain View, Calif.

[73] Assignee: Leonard Bloom, Towson, Md. ; a part interest

[21] Appl. No.: 347,814

[22] Filed: May 4, 1989

Related U.S. Application Data

[63] Continuation-in-part of Ser. No. 233,367, Aug. 18, 1988, which is a continuation-in-part of Ser. No. 105,030, Oct. 6, 1987, Pat. No. 4,774,950.

[51] Int. Cl.⁵ .............................................. A61N 1/00
[52] U.S. Cl. ........................ 128/419 D; 128/419 PG
[58] Field of Search ......... 128/419 P, 419 PG, 419 D

[56]  References Cited
U.S. PATENT DOCUMENTS

| | | | |
|---|---|---|---|
| 4,467,807 | 8/1984 | Bornzin | 128/419 PG |
| 4,730,389 | 3/1988 | Baudino et al. | 128/419 P |
| 4,763,655 | 8/1988 | Wirtzfeld et al. | 128/419 PG |
| 4,799,820 | 8/1988 | Wirtzfeld et al. | 128/419 PG |
| 4,803,987 | 2/1989 | Calfee et al. | 128/419 PG |

Primary Examiner—Francis Jaworski
Assistant Examiner—George Manuel
Attorney, Agent, or Firm—Leonard Bloom

[57] ABSTRACT

A system for and method of treating a malfunctioning heart is based on hemodynamics, the O₂ in blood at a site in a patient's circulatory system being sensed. A signal is developed representative of short term O₂ level in the blood at the sites preferably at a site (right ventricle or a pulmonary artery) which carries mixed venous blood. A signal representative of a baseline O₂ level (fixed or varying) is provided and if the short term current O₂ level differs therefrom by a predetermined value, an indication of possible hemodynamic compromise, cardioversion/-defibrillation is effected. In a second embodiment, the determination of whether the difference between fixed or varying baseline O₂ level or current O₂ level is undertaken after a rate criteria (for example a heart rate above 155 b.p.m.) has been met. In a third embodiment, the rate and O₂ level criteria both must exist at the same time, before cardioverting/-defibrillation is initiated. In a fourth embodiment, a microprocessor is used. The system may be integrated with antitachycardia and/or antibradycardia pacemakers.

67 Claims, 22 Drawing Sheets

CONFER FIG. 5B

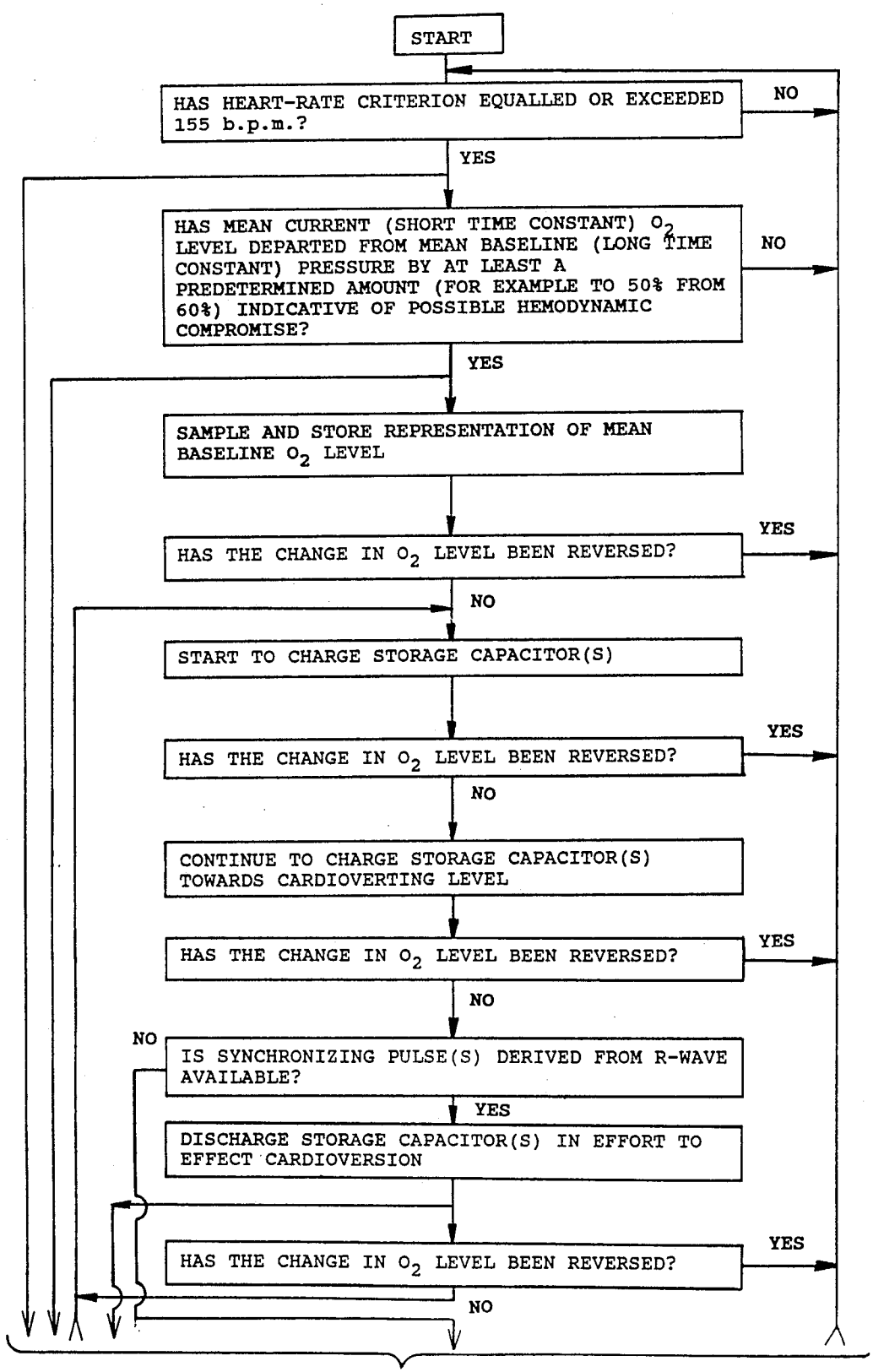
CONFER FIG. 7B    FIG. 7A

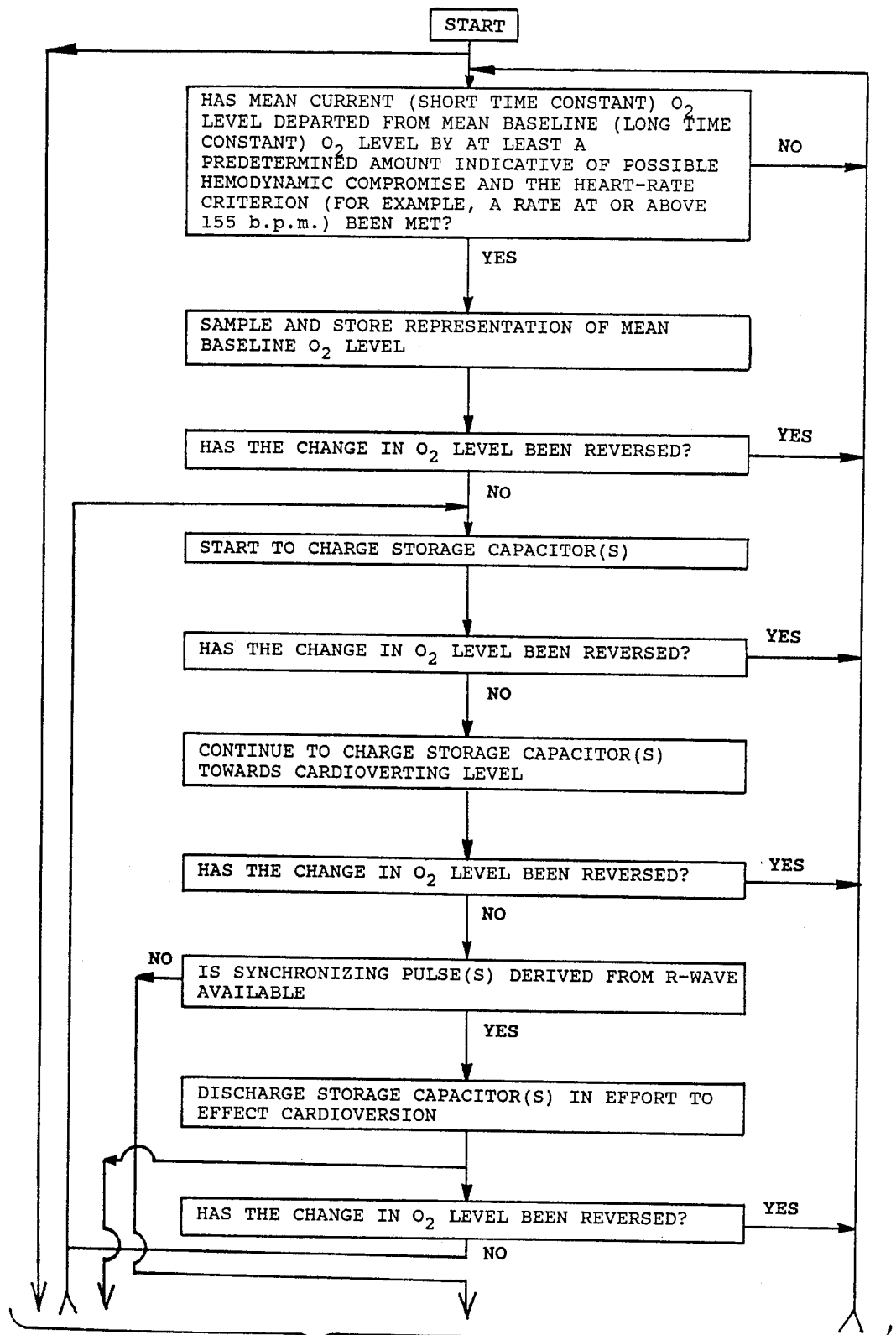

CONFER FIG. 14B

$O_2$ LEVEL RESPONSIVE SYSTEM FOR AND METHOD OF TREATING A MALFUNCTIONING HEART

CROSS REFERENCE TO RELATED APPLICATION

This application is a continuation-in-part of copending application Ser. No. 233,367 of Todd J. Cohen filed Aug. 18, 1988 and entitled "Hemodynamically Responsive System for and Method of Treating a Malfunctioning Heart" which is a continuation-in-part of Ser. No. 105,030 of Todd J. Cohen filed on Oct. 6, 1987 and entitled "Hemodynamically Response System for and Method of Treating a Malfunctioning Heart", which has matured as U.S. Pat. No. 4,774,950 granted Oct. 4, 1988. The disclosures of the two prior applications are incorporated herein in their entirety respectively by reference.

BACKGROUND OF THE INVENTION

1. Field of the Invention

This invention relates to a system for and method of treating a malfunctioning heart and, more particularly, to such a system and method which effects cardioversion/defibrillation in response to sensing a heart malfunction. The invention provides for the cardioverting/defibrillation of a malfunctioning heart as well as the possibility of overcoming a tachycardia manifestation without resorting to either cardioverting or defibrillating the heart.

2. Description of the Prior Art

In recent years, substantial progress has been made in pacemakers and in the development of cardioverting/defibrillating techniques for effectively treating various heart disorders and arrhythmias. Past efforts have resulted in the development of implantable electronic pacemakers and standby cardioverters-defibrillators which, in response to the detection of an abnormal cardiac rhythm, discharge sufficient energy via electrodes connected to the heart to depolarize and restore it to normal cardiac rhythm. An early example of this cardioverting/defibrillating technique is disclosed in U.S. Pat. No. 3,942,536 of Mirowski et al., the technique involving responses to a sensed peak right ventricular systolic pressure dropping to a fixed predetermined threshold level. This known technique did not involve mean pressure changes in either direction from a baseline. Nor did it involve sensing of pressure within any vessels which extends between the heart and lung(s).

Efforts have also been directed toward developing techniques for reliably monitoring heart activity in order to determine whether cardioversion/defibrillation are desirable or necessary. Such techniques include monitoring ventricular rate or determining the presence of fibrillation on the basis of a probability density function (PDF). A system using the PDF technique statistically compares the location of points of a cardiac waveform with the expected locations of points of the normal waveform. When the waveform becomes irregular, as measured by its probability density function, an abnormal cardiac function is suggested. The latter technique is described in U.S. Pat. Nos. 4,184,493 and 4,202,340 both of Langer et al.

A more recent system, as disclosed in U.S. Pat. No. 4,475,551 of Langer et al. utilizes both the PDF technique to determine the presence of an abnormal cardiac rhythm and a heart rate sensing circuit for distinguishing between ventricular fibrillation and high rate tachycardia (the latter being indicated by a heart rate above a predetermined minimum threshold), on the one hand, and normal sinus rhythm or a low rate tachycardia (indicated by a heart rate falling below a pre-determined minimum threshold), on the other hand.

Still further, research in this area has resulted in the development of a heart rate detector system which accurately measures heart rate from a variety of different electrocardiogram (ECG) signal shapes. One such system is disclosed in U.S. Pat. No. 4,393,877 of Imran et al.

Despite these past efforts and the level of achievement prevalent among prior art systems, there are potential difficulties and drawbacks which may be experienced with such devices.

Currently antitachycardia systems detect arrhythmias primarily by sensing rate and perform inadequately in the differentiation of hemodynamically stable from unstable rhythms. These devices, for example, may fire during a stable supraventricular tachycardia (SVT) inflicting pain and wasting energy; damage to the heart may result.

A commonly used implantable antitachycardia device is the automatic implantable cardioverter-defibrillators (AICD) which is commercially available under the model designations 1500, 1510 and 1520 from Cardiac Pacemakers, Inc. whose address is: 4100 North Hamlin Avenue, St. Paul, Minn. 55164. These devices continuously monitor myocardial electrical activity, detecting ventricular tachycardia (VT) and ventricular fibrillation (VF), and delivering a shock to the myocardium to terminate the arrhythmia. The AICD has been shown to reduce the mortality rate in patients with malignant arrhythmias with initial studies at Johns Hopkins Hospital and Stanford Medical Center demonstrating a 50 percent decrease in the anticipated total incidence of death, as reported by Mirowski et al., "Recent Clinical Experience with the Automatic Implantable Cardioverter-Defibrillator", Medical Instrumentation, Vol. 20, pages 285–291 (1986). Arrhythmias are detected by (1) a rate (R wave) sensor and (2) a probability density function (PDF) which defines the fraction of time spent by the differentiated electrocardiogram between two amplitude limits located near zero potential. Presently, the functional window of the PDF is wide to permit the detection of both VT and VF, and therefore, this device functions essentially as a rate-only sensing system. As reported by Mirowski, "The Automatic Implantable Cardioverter-Defibrillator: An Overview", *JACC*, Vol. 6, No. 2, pages 461–466, (Aug., 1985), when an arrhythmia fulfills either the rate or PDF criteria, the device delivers Schuder's truncated exponential pulse of 25 Joules some 17 seconds after the onset of the arrhythmia. The device can recycle as many as three times if the previous discharge is ineffective with the strength of the second, third and fourth pulses being increased to 30 Joules. After the fourth discharge, approximately 35 seconds of nonfibrillating rhythm are required to reset the device. The Mirowski et al., supra, and the Mirowski, supra publications set out, in summary form, background material relating to the defibrillating/cardioverting arts against which the present invention was made.

In addition to the standard automatic implantable cardioverter-defibrillator characterized by the above-noted, dual detection algorithm, a variant of the device which features a sensing system that relies only on the analysis of heart rate is also available. This "rate-only" version of the known cardioverter-defibrillator preferred by some investigators, is more sensitive than the dual detection version unit and theoretically less likely to miss ventricular tachycardias with narrow QRS complexes. It is believed that the "rate-only" system, on the other hand, may be too sensitive, delivering cardioverting/defibrillating pulses too often or too soon, no $O_2$ level parameter having been taken into consideration.

One problem with current systems is that they function primarily as a rate-only sensing systems and may fire for nonmalignant as well as malignant tachycardias. These firings are not benign; potentially endangering myocardium, wasting energy and inflicting pain on the conscious patient, all distinct shortcomings and disadvantages.

SUMMARY OF THE INVENTION

The principal object of the present invention is to provide a system for cardioverting/defibrillating which avoids unnecessary firings, thereby reducing the danger to the myocardium, saving energy and avoiding pain.

Another object of the present invention is to provide an implantable system for cardioverting/defibrillating which avoids unnecessary firings, thereby reducing the danger to the myocardium, saving energy and avoiding pain.

A further object of the present invention is to provide a system for cardioverting/defibrillating which is responsive to change in $O_2$ level in blood within a site in the circulatory system of a patient from a baseline $O_2$ level in blood at the site.

An additional object of the present invention is to provide a system for cardioverting/defibrillating which is responsive to change in $O_2$ level in blood at a site in the circulatory system from a baseline $O_2$ level in blood at the site and to rate criteria.

Yet another object of the present invention is to provide a method of cardioverting/defibrillating which may be advantageously carried out using a cardioverter-defibrillator constructed in accordance with the present invention.

Yet a further object of the present invention is to provide a method of cardioverting/defibrillating which avoids unnecessary firings thereby reducing the danger to the myocardium, saving energy and avoiding pain.

In accordance with preferred embodiments of the present invention, new sensing algorithms are proposed using change in $O_2$ level and/or rate criteria, the latter being taken in series or parallel. The series configuration algorithms could be effected by detecting rate with an intracardiac, extracardiac, or body-surface R-wave sensor. When rate exceeds the programmed cut-off value, at least one parameter, including $O_2$ level in blood at a site in the circulatory system would be monitored to determine its deviation from a fixed or varying baseline level.

Two parallel configuration algorithms in which rate and $O_2$ level criteria function simultaneously are also proposed. Either configuration of algorithm could be adapted to a single catheter carrying $O_2$ sensor in either the pulmonary artery or right ventricle and an R-wave sensing electrode or pair of electrodes at the catheter tip in the right ventricle. The information derived from a Swan-Ganz catheter (already present in the intensive/cardiac care unit patients) could be integrated together with the electrocardiogram to provide a temporary automatic antitachycardia system. Cardioversion/defibrillation could be administered using externally applied patches. Even a noninvasive $O_2$ level responsive antitachycardia system is potentially feasible using doppler technology. The PDF (narrow window of function) and the rate/$O_2$ sensing algorithm could be used simultaneously such that if the rate/$O_2$ level criteria are satisfied (indicating patient significant comprising SVT or VT) the device cardioverters and if the PDF criteria is satisfied indicating (VF) defibrillation results. This pulse delivery system could also be incorporated into a single catheter.

It is to be appreciated that when the $O_2$ level criteria is not met, but the rate criteria indicates tachycardia is present, an antitachycardia pacemaker could be enabled in an effort to correct the malfunction.

A rate/$O_2$ level sensing algorithms could also help integrate a cardioverter-defibrillator with an antitachycardia pacemaker. The change in $O_2$ level would determine which of these devices to engage. For example, when a significant tachycardia as determined by change in $O_2$ level is detected the cardioverter/defibrillator would be used to terminate the arrhythmia. When a stable tachycardia is sensed the antitachycardia pacemaker would attempt to terminate the arrhythmia using such methods as overdrive, burst, or extra stimulus pacing, incremental or decremental scanning, or ultra-high frequency stimulation. If the tachycardia was accelerated, this would be detected by the rate/$O_2$ level sensing algorithm and cardioverted or defibrillated. With a pacemaker present, a bradycardia failsafe could be built into the system.

The adaptation of a $O_2$ level parameter to the sensing system of antitachycardia devices appears to be a logical improvement to its present function.

From one viewpoint, the invention can be viewed as being in a system for treating a malfunctioning heart of the type which includes storage means for storing electrical energy. Electrode means electrically couple the storage means to the heart, sensing means being provided for sensing $O_2$ level in blood within a site in a circulatory system. Means provide a first signal representative of baseline $O_2$ level. This baseline may be fixed or variable. Means responsive to output from the sensing means develop a second signal representing current $O_2$ level in blood at the site over a period of given duration. Means responsive to output from the means for providing the first signal and output from the means for developing the second signal are provided for charging and enabling discharge of the electrical energy stored by the storage means across the electrode means upon change in the current $O_2$ level in blood at the site of at least a predetermined amount from the representative baseline $O_2$ level in blood.

In its method aspect the invention can be seen as a method of treating a malfunctioning heart which includes sensing $O_2$ level in blood at a site of a circulatory system, providing a representation of baseline $O_2$ level (which in different embodiments can be fixed or varying) and determining current $O_2$ level in blood at the site from the sensed level at the site over a period of given duration. The method provides for delivering cardioverting/defibrillating electrical energy to the heart in response to change of at least a predetermined magnitude in the current $O_2$ level in blood at the site from the baseline $O_2$ level.

The invention also can be seen as being in a system for treating a malfunctioning heart of the type which includes storage means for storing electrical energy and electrode means for electrically coupling the storage means to the heart. Sensing means sense $O_2$ level in blood at a site in a circulatory system, while means provide a first signal representative of baseline $O_2$ level (fixed or variable) in blood at the site. Means are provided for developing a second signal representing current $O_2$ level in blood at the site. Means responsive to output from the means for providing the first signal and output from the means for developing the second signal are provided for charging and enabling discharge of the electrical energy stored by the storage means across the electrode means upon change in the current $O_2$ level at the site of at least a predetermined amount from the representative baseline $O_2$ level in blood at the site.

The invention can also be viewed as a method of treating a malfunctioning heart comprising sensing $O_2$ level in blood within a site in a circulatory system and providing a representation of baseline $O_2$ level (either fixed or varying) in blood at the site. Determining current $O_2$ level in blood at the site from the sensed level is a salient step. Electrical energy is delivered to the heart in response to change of at least a predetermined magnitude in the current $O_2$ level in blood at the site from the baseline $O_2$ level.

From a slightly different viewpoint, the invention can be seen as a system for treating a malfunctioning heart comprising sensing means for sensing $O_2$ level in blood within a site in a circulatory system and means for providing a first signal representative of baseline $O_2$ level (either fixed or varying) in blood at the site. Means responsive to output from the sensing means develop a second signal representing current $O_2$ level in blood at the site. Means responsive to output from the means for providing the first signal and output from the means for developing the second signal enable electrical means for correcting the malfunction upon change in the current $O_2$ level in blood at the site of at least a predetermined amount from the representative baseline $O_2$ level in blood at the site.

The invention also is a system for treating a malfunctioning heart comprising means for monitoring $O_2$ in blood at a site within a circulatory system to provide an output representing $O_2$ level in blood at the site operatively associated with means responsive to the output for supplying a malfunction correcting input to the heart upon the $O_2$ level in blood at the site falling to or below a compromising level.

In its method aspects, the invention can be seen as a method of treating a malfunctioning heart comprising continuously monitoring $O_2$ level in blood at the site, and delivering a malfunctioning correcting input to the heart upon the $O_2$ level in blood at the site falling to or below a compromising level.

The novel features that are considered characteristic of the invention in its method and system aspects are set forth with particularity in the appended claims. The invention itself, however, both as to its organization and its method of operation, together with other objects and advantages thereof is to be understood from the following description of illustrative embodiments, when read in conjunction with the accompanying drawings, wherein like reference numerals refer to like components.

BRIEF DESCRIPTION OF THE DRAWINGS

FIGS. 7A and 7B constitute a second exemplary flowchart of a series of actions or steps which may be carried out by the system illustrated in FIG. 6 and effect achievement of a corresponding method.

FIGS. 9A and 9B constitute a third exemplary flowchart of a series of actions or steps which may be carried out by the system illustrated in FIG. 8 and effect achievement of a corresponding method.

DETAILED DESCRIPTION OF THE PREFERRED EMBODIMENTS

Figure 1:
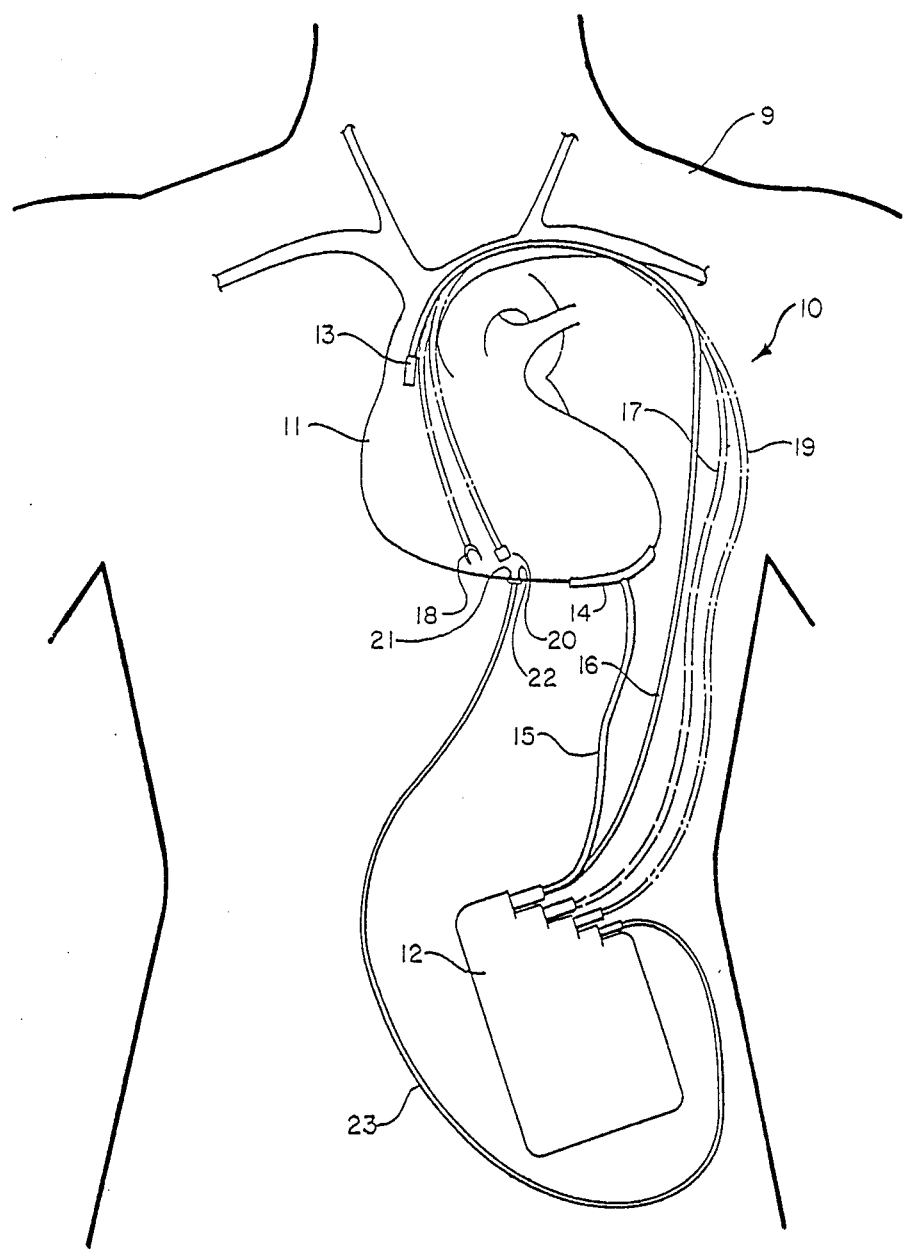
FIG. 1 is a diagrammatic, generalized illustration of an exemplary, implanted $O_2$ responsive system for treating a malfunctioning heart.

As shown in FIG. 1, an exemplary embodiment of an automatic implantable cardioverter-defibrillator system is designated generally by the numeral 10 and illustrated diagrammatically as being implanted within a human subject 9. The cardioverter-defibrillator system 10 includes an implanted housing 12 within which major circuit components of the system are housed. A first electrode 13 is positioned within the heart 11 of the subject 9, the details of placement and nature of the first electrode being more specifically shown in FIGS. 2A and 2B to which reference is to be made below. A second electrode, illustrated as a patch electrode 14 is positioned on the outside of the heart 11 at the apex thereof. The pair of electrodes 13, 14 are provided for the purpose of delivering D.C. cardioverting/defibrillating energy from within the housing 12 to the heart 11 under control of circuitry within the housing, a pair of insulated leads 16 and 15 respectively being provided for this purpose. A pair of rate sensing electrodes 18 are provided within the heart 11, these electrodes being positioned in tissue and being conductively coupled to circuitry within the housing 12 via an insulated cable 17. A further pair of leads extend from the light responsive sensor 20, which is to sense O₂ level in mixed venous blood, to circuitry within the housing 12 via an insulated cable 19. It is to be understood that the insulated leads 15 and 16, the insulated cable 17 (or the pair of leads therein), and the insulated cable 19 (or the fiberoptic bundles 19a, 19b therein) can all be incorporated into a single cable, the electrode 13, the rate sensing electrodes 18 and the O₂ sensor 20 being carried by and forming parts of a catheter Pacemaking circuitry within the housing 12 may be provided to produce antitachycardia pacemaking signals, to a pair of pacing electrodes 21 and 22, illustrated as being fixed in tissue on the right-side of the heart. The pacing electrodes 21 and 22 are connected by respective conductive leads within a cable 23 which communicates with circuitry within the housing 12.

Figure 2:
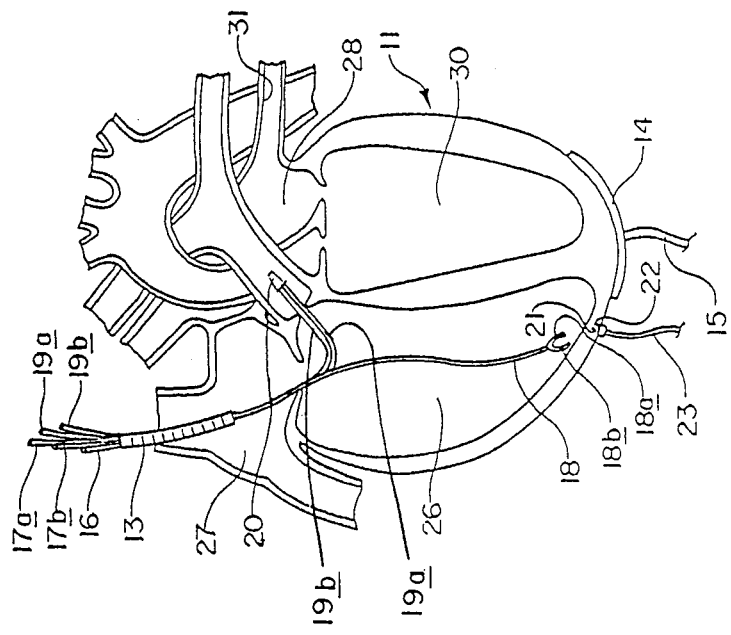
FIG. 2A is an illustration of one catheter positioned within a heart, a light responsive sensor, which in effect senses $O_2$ level, being associated with the catheter and shown positioned inside the right ventricle.
FIG. 2B is an illustration of a second catheter positioned within a heart, a light responsive sensor, which in effect senses $O_2$ level, being associated with the catheter and shown positioned within a pulmonary artery.
Figure 2:
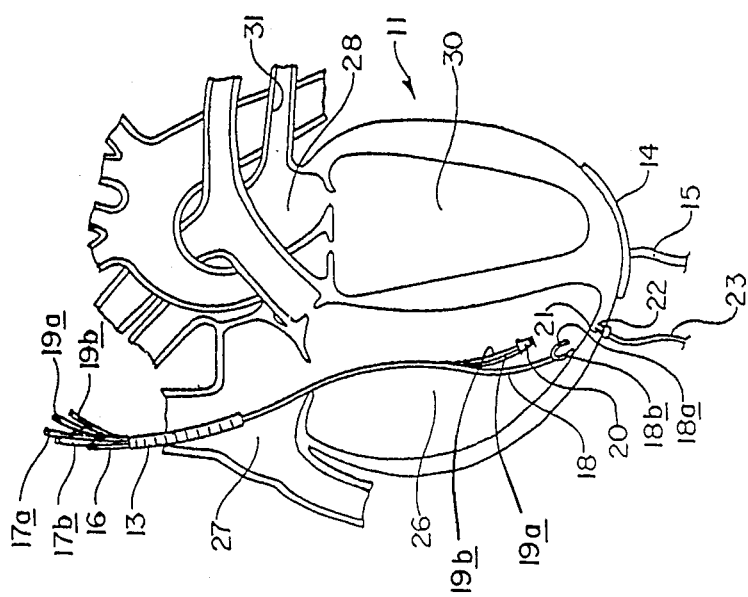

Turning to FIG. 2A, a more detailed illustration of the heart 11 of a subject, shows the heart in somewhat more detail and in section so that placement of parts of the system within the heart 11 can be seen in more detail, albeit diagrammatically. The heart 11 as illustrated includes a right ventricle 26, a right atrium 27, a left atrium 28 and a left ventricle 30. The electrode 13 is positioned within the superior vena cava. It is to be understood that the patch electrode 14, which cooperates with the electrode 13, could also be modified into a different form so it too could be positioned within the heart. The electrode 13 could be replaced with a patch electrode so that it also could be positioned on the surface of the heart, without departing from the present invention. The electrodes 13 and 14, in cases not involving implantation, could be replaced with conventional paddle electrodes or other external, body engaging electrodes, again without departing from the present invention. Thus, the invention could be used as a temporary measure for patient care in intensive care units and the like.

As illustrated in FIG. 2A, the pacing electrodes 21 and 22 are shown as being positioned on the exterior wall of right ventricle 26 for the purpose of illustration; these pacing electrodes could be placed elsewhere on or within the heart 11 in accordance with the needs of individual patients, taking into account the best particular location most suitable for correcting or overcoming the particular malfunction involved, the condition of the individual patient and his or her heart being taken into account.

Heart rate wave (R-wave) sensing electrodes 18a and 18b are illustrated as being positioned near the apex of the heart 11 within the right ventricle 26, for purposes of illustration. Other locations are equally well suited; again, the selected location being chosen with the condition of the particular patient and his or her heart in mind. The electrodes 18a and 18b are conductively connected to the circuitry within the housing 12 via leads 17a and 17b within the cable 17 (FIG. 1).

The light responsive O₂ level sensor 20, as illustrated in FIG. 2A, is positioned within the right ventricle 26. The O₂ light responsive sensor 20 can be one of a number of commercially available sensors; one such sensor is used as part of a fiberoptic catheter available under the designations 5032-01 and 5037-01 from Abbott Critical Care, Inc., of 1212 Terra Vella Avenue, Mountain View, Calif. 94043. These catheters have been associated with an oxiometer computer also available from Abbott Critical Care, Inc. under the designation 50130-01 for the purpose of measuring cardiac output and the like. The sensor 20 is carried on the end of the catheter and positioned within the right ventricle 26. Fiberoptic bundles 19a, 19b within the cable 19 provide light conduits respectively into the right ventricle 26 and out from the right ventricle, as is known. The light carried into the right ventricle 28 by the fiberoptic bundle 19a is reflected by the red blood corpuscles in the mixed venous blood and returned via the fiberoptic bundle 19b. It is to be appreciated that rather than reflection of light, refraction or transmission could be used to achieve similar results. The source of light may be, as is known in the above-mentioned system of Abbott Critical Care, Inc., an LED. Preferably, the light from the LED has three specific wavelengths in the red spectrum, as in the system of Abbott Critical Care, Inc. The transmitted, reflected or refracted light could be passed through filters to pass substantially the three frequencies, while attenuating the other frequencies, if desired. It is believed that noncoherent monochromic red light would be suitable in proposed embodiments. A D.C. voltage signal representative of the actual, instant O₂ level in mixed venous blood within the right ventricle 26 is developed by the circuitry within the implanted housing 12 (FIG. 1). The intensity of the light returned via the fiberoptic bundle 19b is directly related to the O₂ content of the mixed venous blood in the right ventricle 26.

As illustrated in FIG. 2B the heart 11, as well as the components of the system of the present invention, other than the position of the light responsive O₂ sensor 20, correspond to the heart 11 and the system components as shown in FIG. 2A. The placement of the sensor 20 differs in FIG. 2B. As shown in FIG. 2A, the light responsive O₂ sensor 20 provides, as its output, a light intensity output corresponding to the level of O₂ being carried by the mixed venous blood in the right ventricle 28. One can expect that a healthy adult human will have in his or her right ventricle an $O_2$ level in the range of from about 60% to about 80%, based on a fully saturated level of about 98% (virtually 100%) in the arterial blood. Were the $O_2$ level in the mixed venous level to fall below about 50%, for example, the individual may be in an $O_2$ level related compromised condition. As shown in FIG. 2B the light responsive $O_2$ sensor 20 is positioned within a pulmonary artery to sense mixed venous blood in the major pulmonary artery. It is to be appreciated that the sensor 20 could be positioned in other ones of pulmonary arteries, if desired.

Figure 3:
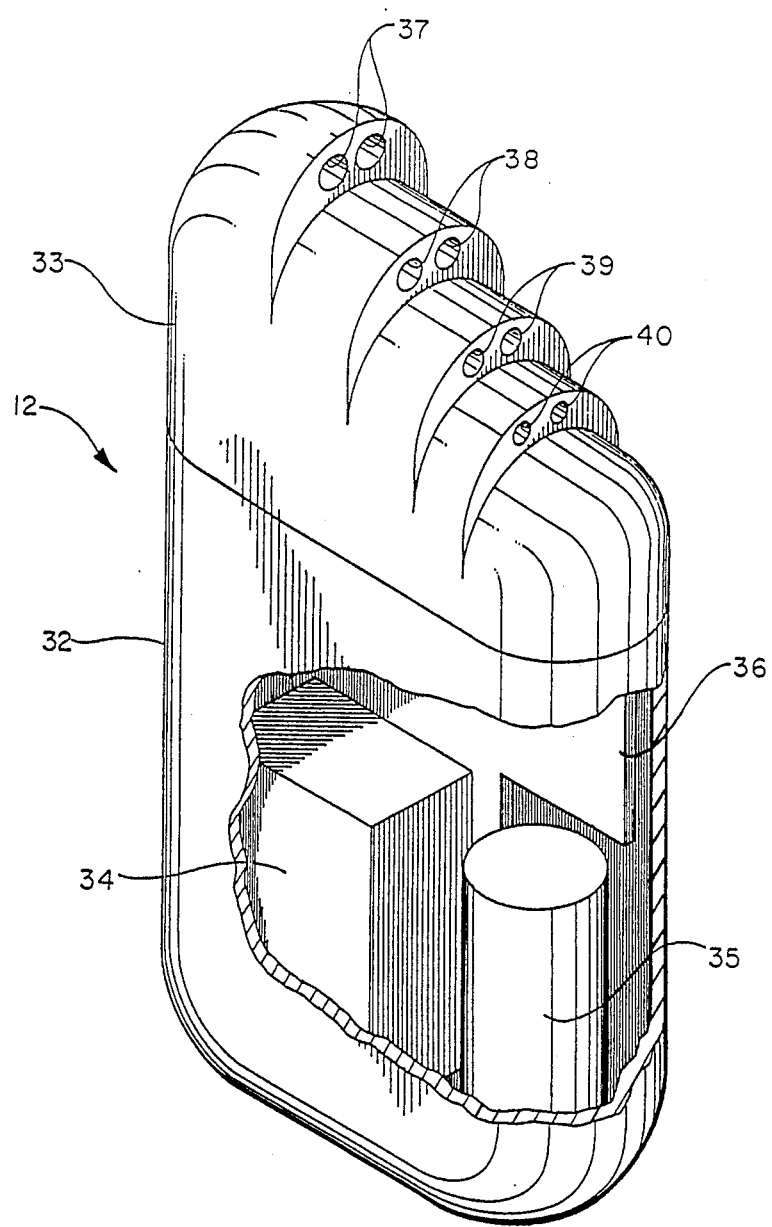
FIG. 3 is a pictorial illustration of an exemplary implantable controllable cardioverting/defibrillating electrical energy generator which may be used in practicing the present invention, the housing of the generator being partially broken away to show positioning of major components thereof.

One possible general implantable configuration of the housing 12 is shown in FIG. 3. The housing 12 includes a case 32, made of titanium, and a header 33, formed of an epoxy material, fixed to the case 32, all external components being hermetically sealed and biocompatible for human implantation. Within the case 32 is a battery pack or battery 34, an energy storage capacitor 35 and an electronic module 36 in or on which circuit components, other than the battery pack or battery 34 and the capacitor 35, are positioned. Detailed embodiments of exemplary circuits which are in or on or connected to the module 36 are illustrated in FIGS. 4, 6, 8 and 10, to which reference is made hereinbelow. A plurality of pairs of receptacles 37-40 are shown in the header 33 for receiving corresponding pairs of electrical leads which are respectively within the insulated cables 15, 16 and 17 and 23 (FIG. 1). Cable 19 carries within the respective fiberoptic bundles 19a and 19b (FIG. 1).

Figure 4:
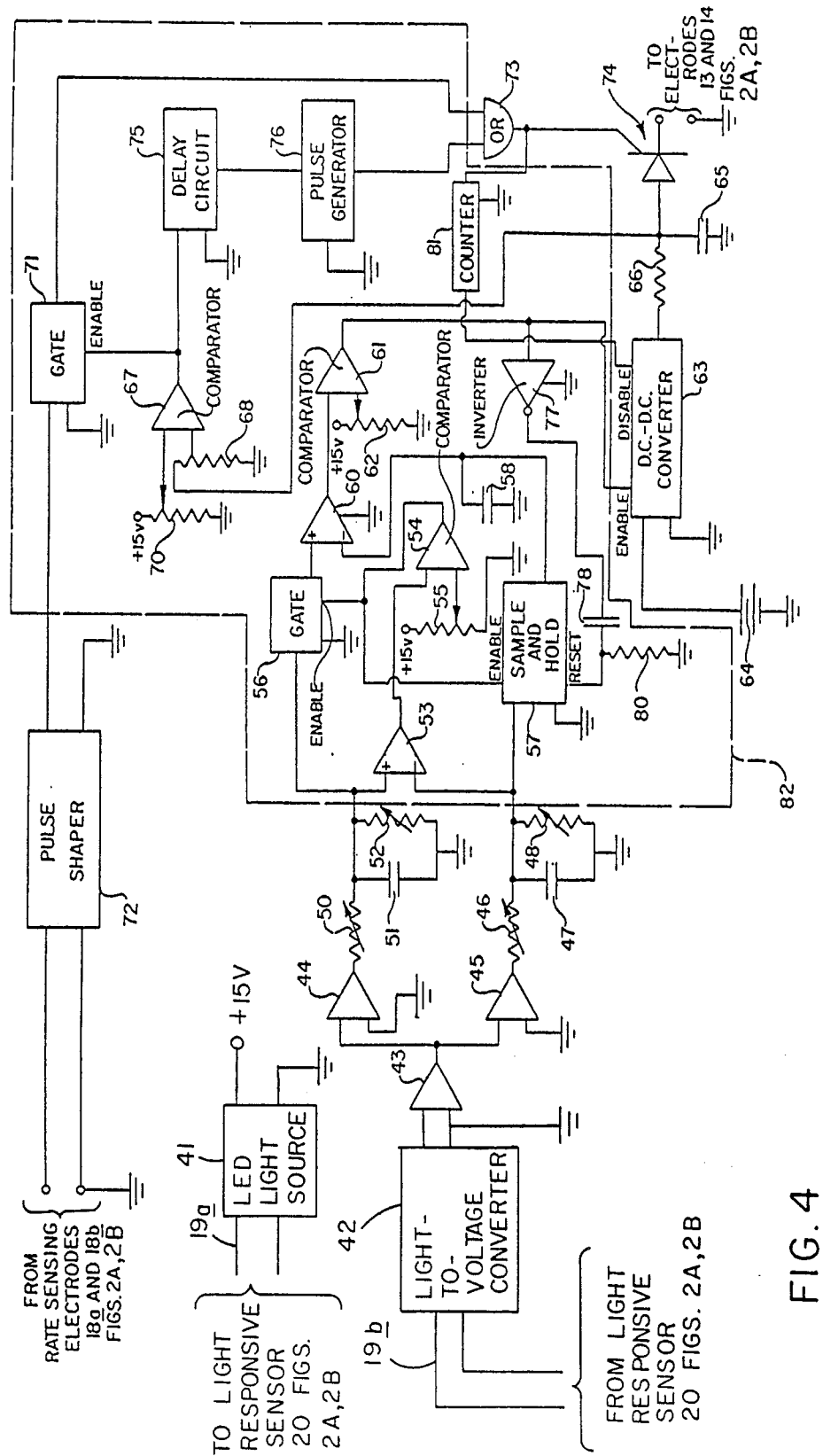
FIG. 4 is a partially block, schematic diagram of a $O_2$ responsive system for treating a malfunctioning heart which is responsive to $O_2$ level in mixed venous blood.

Turning to FIG. 4, an exemplary embodiment of the circuit components, which may be positioned within the housing 12 (FIGS. 1 and 3), includes a LED light source 41 which produces red light (including the three frequencies mentioned above), and the light being carried by the fiberoptic bundle 19a to the sensor 20 (FIGS. 2A, 2B). The light, after reflection from red blood corpuscles in mixed venous blood is returned, via the fiberoptic bundle 19b to a light-to-voltage converter 40 42 which produces a varying D.C. voltage output which corresponds to the $O_2$ level of the mixed venous blood. The variable D.C. voltage output signal from the converter 42 representing $O_2$ level is fed to an amplifier 43, which amplifies the $O_2$ level representing D.C. input signal and feeds the same to respective buffer amplifiers 44 and 45. The circuit of FIG. 4, as illustrated, is suitable for treating a malfunction heart using the $O_2$ level only criteria.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage across the capacitor 47 represents the mean $O_2$ level sensed by the sensor 20 (FIGS. 1, 2A and 2B) and over a relatively long period, for example during the preceding fifteen (15) minutes or even longer (for example a number of hours) or shorter (for example one hundred twenty (120) seconds) being suitable in some cases. The resistors 46 and 48 may be set by a medical professional to suit the particular patient involved, so far as what the most suitable period length (period of predetermined length) for baseline $O_2$ data acquisition appears to be most suitable. The D.C. voltage (first signal) which appears across the capacitor 47 thus represents a long term mean baseline $O_2$ level of mixed venous blood. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean $O_2$ level of mixed venous blood sensed by the sensor 20 (FIGS. 1, 2A and 2B) over a relatively short period, for example, during the preceding fifteen (15) seconds or longer (for example 60 seconds) or shorter (for example six seconds). The resistors 50 and 52 may be set by a medical professional to suit the particular patient involved, so far as what the period length (period of given length) for current data acquisition appears to be most suitable.

As illustrated the long term (baseline) and short term (current) D.C. voltage signals which appear across the respective capacitors 47 and 51 are fed respectively to the inverting and noninverting terminals of an operational amplifier 53, a difference D.C. voltage signal appearing as the output from the operational amplifier 53. The D.C. output signal from the operational amplifier 53 is fed to a first input terminal of a first comparator 54, the second input terminal of the comparator 54 is connected to the wiper of a potentiometer 55 which is connected between ground and a point of fixed D.C. potential, illustrated as being +15 volts, from an internal power supply bus.

Whenever the voltage supplied to the comparator 54 from the operational amplifier 53 exceeds the voltage supplied via the wiper from the potentiometer 55, a low (ZERO) level on the output terminal from the comparator 54 goes high (ONE), the ONE signal being coupled as an enabling input to a gate 56 and to a sample-and-hold circuit 57 which receive, at their respective signal input terminals, the voltage representing current mean $O_2$ level in mixed venous blood appearing across the capacitor 51 and the voltage representing mean baseline $O_2$ level in mixed venous blood appearing across the capacitor 47.

A D.C. output from the sample-and-hold circuit 57 is stored in a storage circuit, for the purpose of illustration shown as a capacitor 58. This stored voltage signal (stored first signal) representing mean baseline (long-term) $O_2$ level in mixed venous blood is supplied to the inverting input terminal of an operational amplifier 60 which has its noninverting input terminal connected to the output terminal of the gate 56, which when enabled, passes the D.C. voltage signal appearing across the capacitor 51 and representing current (short-term) mean $O_2$ level in mixed venous blood to the operational amplifier 60. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of $O_2$ level compromise of the patient, the output terminal of the comparator 61 goes from low (ZERO) to high (ONE) which signal is passed to the enable terminal of a D.C.-to-D.C. converter 63. It is to be understood that the wipers of the potentiometers 55 and 62 are independently adjustable; consequently, the wiper on the potentiometer 62 may be positioned so that the $O_2$ level difference which causes its output to go from ZERO to ONE is slightly greater than $O_2$ level difference which causes the comparator 54 to initiate the enabling functions. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse is a truncated exponential pulse of about 25 Joules delivered approximately 17 seconds from onset of the compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A and 2B) and produces a pulse train in synchronism with the R-wave supplied from the electrodes 18a, 18b. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 into the malfunctioning heart, via the electrodes 13 and 14 (FIGS. 1, 2A and 2B) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65, which by then has charged to a higher level discharges, via the SCR 74 and the electrodes 13 and 14 (FIGS. 1, 2A and 2B), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as described above to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the stored signal representing baseline mean $O_2$ level and the signal representing current mean $O_2$ level returns to an acceptable level, indicating that the $O_2$ level related compromise of the patient has been overcome. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the $O_2$ level (which would cause the output of the comparators 54 and 61 to become ZERO, removing the enable signals from the sample-and-hold circuit 57 and the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

Figure 5A:
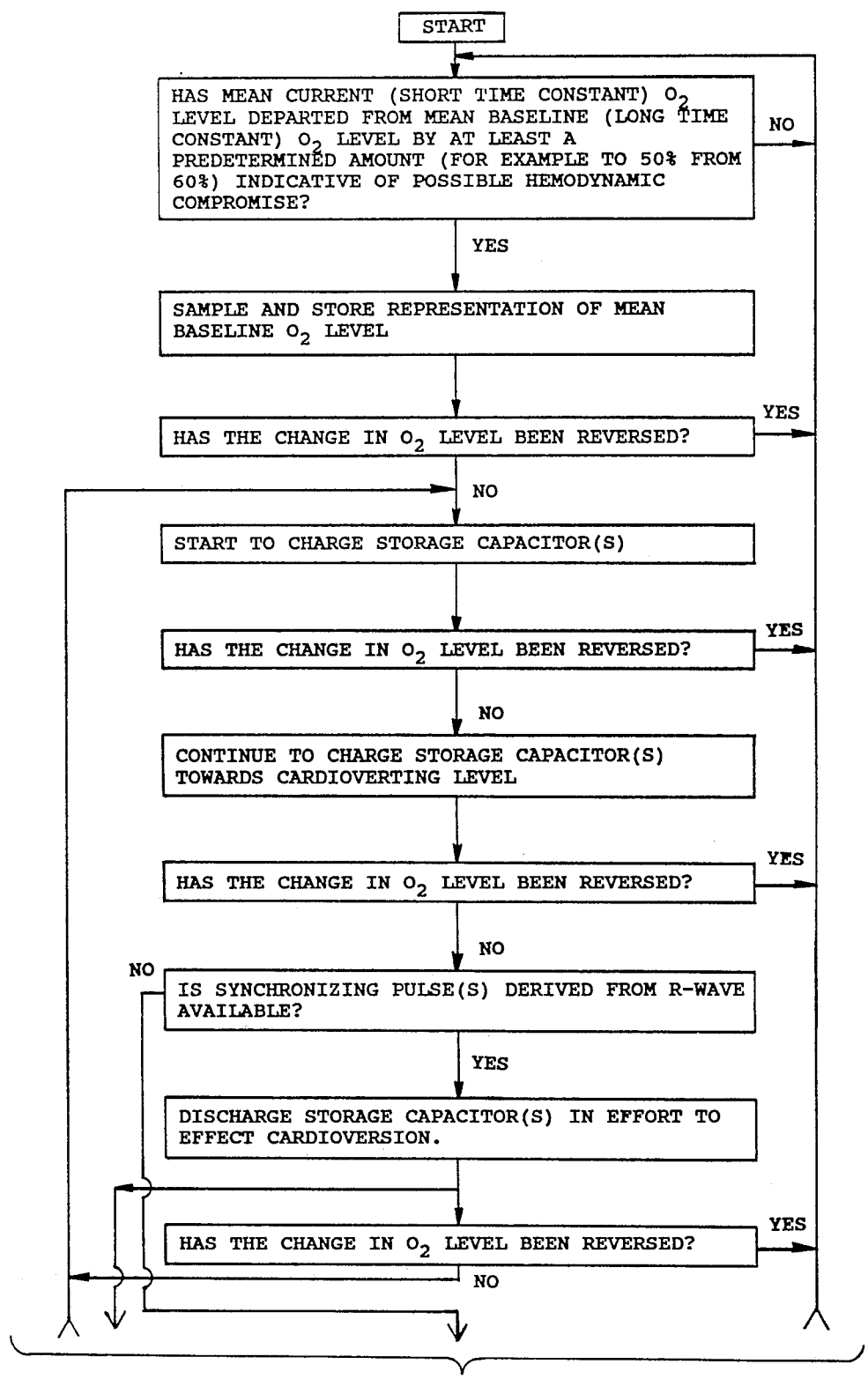
FIGS. 5A and 5B constitute a first exemplary flowchart of a series of actions or steps which may be carried out by the system illustrated in FIG. 4 and effect achievement of a corresponding method.
Figure 5B:
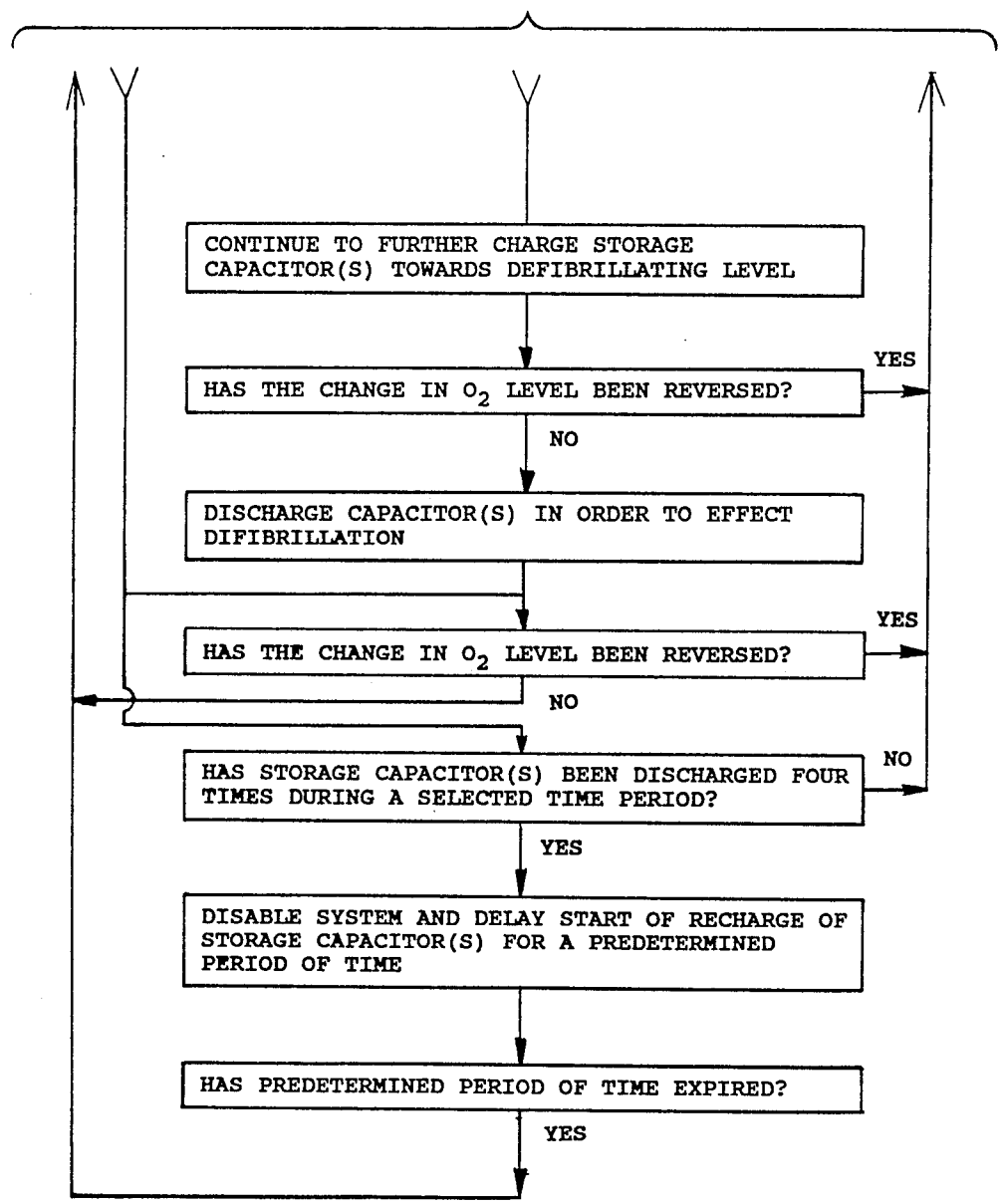

It is to be appreciated that the circuit of FIG. 4 described above may be considered, at least in part, to be a controller or processor, which could be realized as a microprocessor. The processor, with its associated components, in effect carries out the steps set out in the flowchart of FIGS. 5A and 5B.

The circuit of FIG. 4 could be associated with an antitachycardia pacemaker and/or an antibradycardia pacemaker, if desired.

Figure 6:
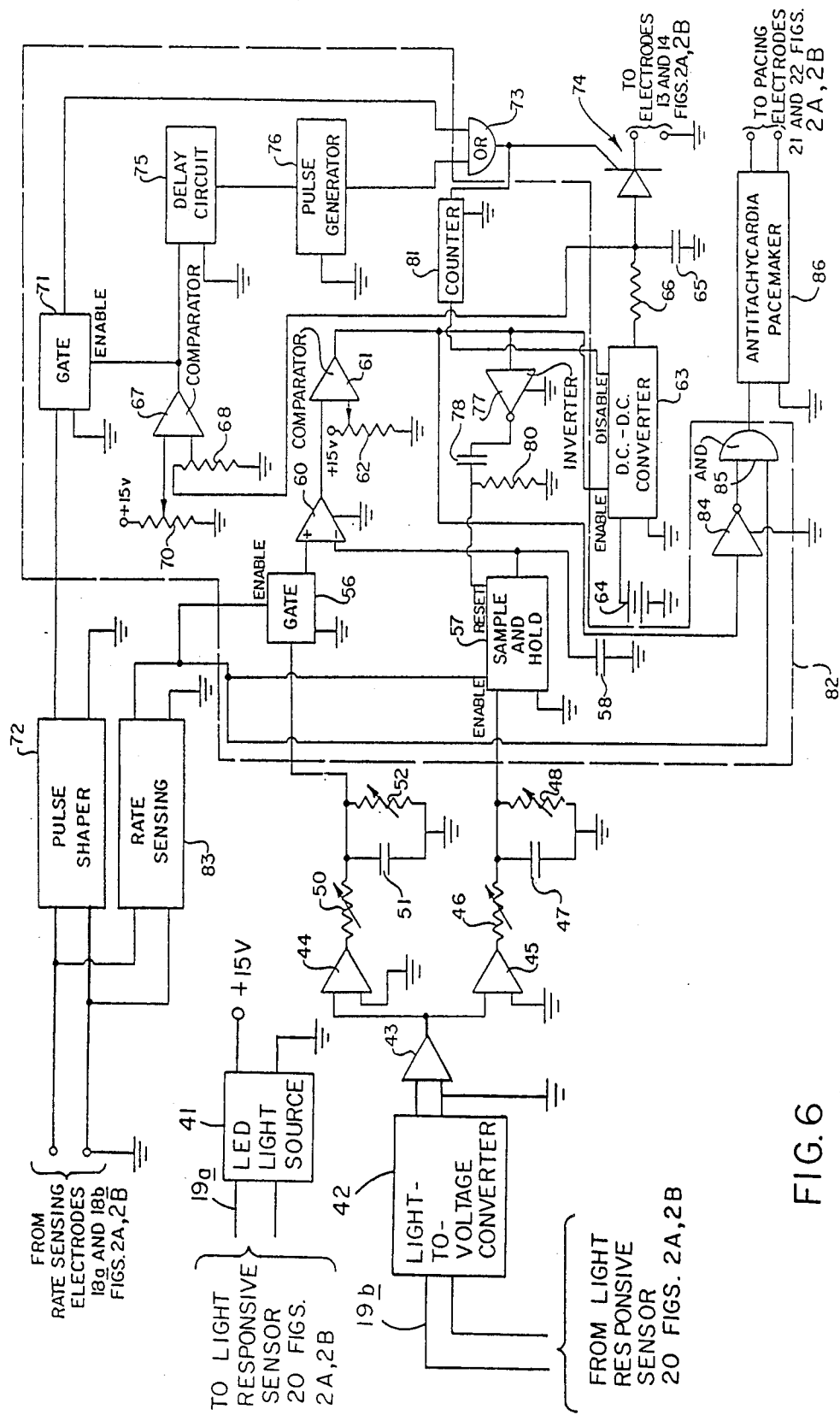
FIG. 6 is a partially block, schematic diagram of a further $O_2$ responsive system for treating a malfunctioning heart which is responsive to $O_2$ levels in mixed venous blood and heart rate.

Turning to FIG. 6, a further exemplary embodiment of the circuit components, which may be positioned within the housing 12 (FIGS. 1 and 3) includes a LED light source 41 which produces red light (including the three frequencies mentioned above), the light being carried by the fiberoptic bundle 19a to the sensor 20 (FIGS. 2A, 2B). The light after reflection from red blood corpuscles in mixed venous blood is returned, via the fiberoptic bundle 19b to the light-to-voltage converter 42. The converter 42 produces a varying D.C. voltage output which corresponds to the $O_2$ level of the mixed venous blood. The variable D.C. voltage output signal from the converter 42 represents the $O_2$ level in the mixed venous blood. The varying D.C. output voltage from the converter 42 is fed to an amplifier 43, which amplifies the $O_2$ level representing D.C. input signal and feeds the same to respective buffer amplifiers 44 and 45. The circuit of FIG. 6, with associated components, is suitable for practicing the present invention in which both O₂ level in mixed venous blood and beating rate criteria are to be taken into account. The rate criterion is examined first and, if met, the O₂ level criteria are then considered.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean O₂ level of mixed venous blood sensed by the light responsive sensor 20 (FIGS. 1, 2A and 2B) over a relatively long period, for example during the preceding fifteen (15) minutes or even longer (for example a number of hours) or shorter (for example one hundred twenty (120) seconds) being suitable in some cases. The D.C. voltage (first signal) which appears across the capacitor 47, thus represents a long term mean baseline O₂ level. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean O₂ level sensed by the sensor 20 (FIGS. 1, 2A and 2B) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the signal input terminal of a sample-and-hold circuit 57 and to the signal input terminal of a gate 56. A rate sensing circuit 83 is arranged to receive a beating rate (R-wave) signal from the rate sensing electrodes 18a, 18b (FIGS. 1, 2A and 2B). Whenever the rate exceeds a given rate, for example 155 beats per minute, indicating tachycardia, the output terminal of the rate sensing circuit 83 goes from low (ZERO) to high (ONE). The ONE signal (first control signal) is supplied as an enabling input to the gate 56 and to sample-and-hold circuit 57. The D.C. voltage representing current mean O₂ level in mixed venous blood appearing across the capacitor 51 is fed via the enabled gate 56 to the noninverting input terminal of an operational amplifier 60. The D.C. voltage representing mean baseline O₂ level in mixed venous blood appearing across the capacitor 47 is transferred to the sample-and-hold circuit 57, appearing across its associated capacitor 58. This stored D.C. voltage representing mean baseline O₂ level in mixed venous blood is supplied to the inverting input terminal of the operational amplifier 60 which has its noninverting input terminal connected to the output terminal of the gate 56 which, when enabled as noted above, passes the D.C. voltage signal appearing across the capacitor 51 and representing current mean O₂ level to the operational amplifier 60.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of O₂ level compromise of the patient, the output terminal of the comparator 61 goes from low (ZERO) to high (ONE) and the signal (second control signal) is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse for cardioversion is a truncated exponential pulse of about 25 Joules delivered approximately 17 seconds from onset of the compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A and 2B) and produces a pulse train in synchronism with the R-wave supplied from the electrodes 18a, 18b. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A and 2B) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce output pulse to initiate defibrillation. The pulse is supplied, via the OR circuit 73, to the gate electrode of the SCR 74 causing the SCR to fire. The energy storage capacitor 65, which during the elapsed three seconds has charged to a higher level, discharges, via the SCR 74 and the electrodes 13 and 14 (FIGS. 1, 2A and 2B), into the malfunctioning heart via the electrodes 13 and 14 (FIGS. 1, 2A and 2B) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean $O_2$ level in mixed venous blood and current mean $O_2$ level in mixed venous blood returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the $O_2$ level by overcoming the $O_2$ level related compromise (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 6, cardioverting/defibrillating D.C. pulses are delivered to the malfunctioning heart only when the rate criterion is first satisfied and, thereafter, the $O_2$ level in mixed venous blood criteria also satisfied. This can be viewed as a series rate-$O_2$ level algorithm.

In the event the rate criterion is met, but the $O_2$ level criteria are not; that is to say no $O_2$ level related compromise presents, the circuit of FIG. 6 nevertheless acts to enable an antitachycardia pacemaker 86 which supplies pacing signals to the pair of pacing electrodes 21, 22 (FIGS. 1, 2A and 2B). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no $O_2$ level related compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

Figure 7B:
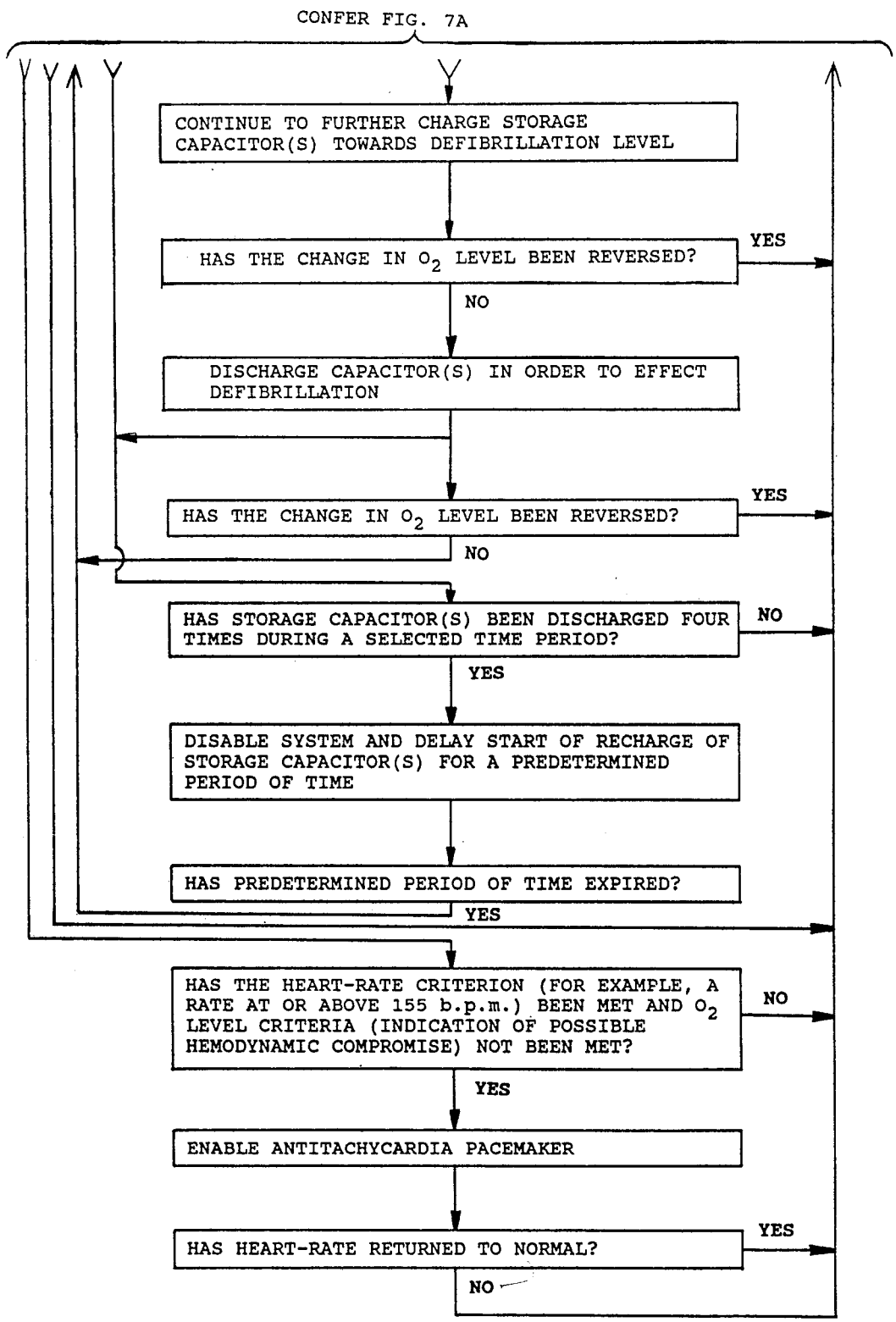

It is to be appreciated that the circuit of FIG. 6 described above may be considered, at least in part, to be a processor, which could be realized as a microprocessor. The processor, with its associated components, in effect carries out the steps set out in the flowchart of FIGS. 7A and 7B.

It is to be understood that the system of FIG. 6 could be associated with a failsafe antibradycardia pacing system, if desired.

Figure 8:
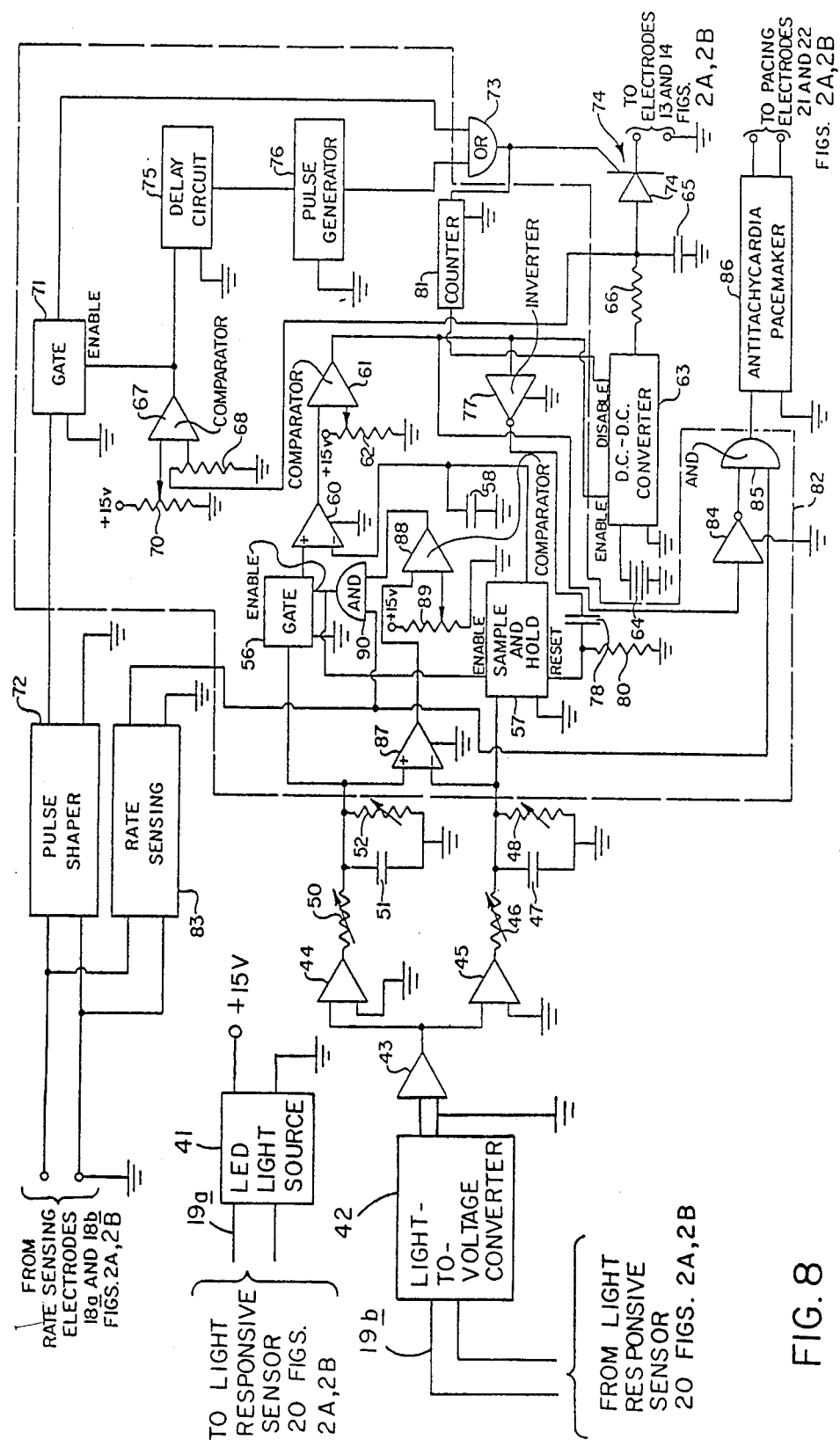
FIG. 8 is a partially block, schematic diagram of $O_2$ responsive system for treating a malfunctioning heart which is a variant of the circuit of FIG. 6.

Turning to FIG. 8, an additional exemplary embodiment of the circuit components, which may be positioned within the housing 12 (FIGS. 1 and 3) includes a LED light source 41 which produces red light (including the three frequencies mentioned above), the light being carried by the fiberoptic bundle 19a to the sensor 20 (FIGS. 2A, 2B). The light after reflection from red blood corpuscles in mixed venous blood is returned, via the fiberoptic bundle 19b to the light-to-voltage converter 42. The converter 42 produces a varying D.C. voltage output which corresponds to the $O_2$ level of the mixed venous blood. The variable D.C. voltage output signal represents $O_2$ level in mixed venous blood. The varying D.C. output voltage from the converter 42 is fed to an amplifier 43, which amplifies the $O_2$ level representing D.C. input signal and feeds the same to respective buffer amplifiers 44 and 45. The circuit of FIG. 8 can be used in practicing the present invention using both rate and $O_2$ level of mixed venous blood as criteria. In this case the rate and $O_2$ level criteria must exist simultaneously to start the sample-and-hold function.

The output from the buffer amplifier 45 is supplied to an RC circuit constituted by an adjustable resistor 46 connected to ground via a series connected capacitor 47 having a large adjustable resistor 48 connected in parallel therewith. The time constants (charging and discharging) of these circuit components are such that the D.C. voltage across the capacitor 47 represents the mean $O_2$ level sensed by the sensor 20 (FIGS. 1, 2A and 2B) over a relatively long period, for example during the preceding fifteen (15) minutes or even longer for example a number of hours) or shorter (for example one hundred twenty (120) seconds being suitable in some cases. The D.C. voltage (first signal) which appears across the capacitor 47 thus represents a long term mean baseline $O_2$ level. The term "mean" as used herein is broad and includes the average value, as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean $O_2$ level sensed by the sensor 20 (FIGS. 1, 2A and 2B) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively to the inverting and noninverting terminals of an operational amplifier 87, a difference D.C. voltage signal appearing as the output from the operational amplifier 87. The D.C. output signal from the operational amplifier 87 is fed to a first input terminal of a comparator 88. The second input terminal of the comparator 88 is connected to the wiper of a potentiometer 89 which is connected between ground and a point of fixed D.C.

potential, illustrated as being +15 volts, from an internal power supply bus.

Whenever the voltage supplied to the comparator 88 from the operational amplifier 87 exceeds the voltage supplied via the wiper from the potentiometer 89, a low (ZERO) level on the output terminal from the comparator 88 goes high (ONE), the ONE signal being coupled to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The ONE signal from the AND gate 90 is also fed as an enabling input to a sample-and-hold circuit 57. The voltage representing current mean $O_2$ level in mixed venous blood appearing across the capacitor 51 is fed to the noninverting input terminal of an operational amplifier 60. The voltage representing mean baseline $O_2$ level in mixed venous blood appearing across the capacitor 47 is fed to the sample-and-hold circuit 57.

A D.C. output from the sample-and-hold circuit 57 is stored in a storage circuit, for the purpose of illustration shown as a capacitor 58. This stored voltage is supplied to the inverting input terminal of the operational amplifier 60 which has its noninverting input terminal connected to the output terminal of the gate 56, which when enabled, passes the D.C. voltage signal appearing across the capacitor 51 and representing current mean $O_2$ level to the operational amplifier 60. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of $O_2$ level compromise, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the compromise must get worse than it was when the sample-and-hold circuit 57 is enabled before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65, via a resistor 66 towards the high voltage. The capacitor 65 is of such size that it will store energy levels sufficient to produce the desired cardioverting/defibrillation pulses. The desired pulse for effecting cardioversion is a truncated exponential pulse of about 25 Joules delivered approximately 17 seconds from onset of the compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A and 2B) and produces a pulse train in synchronism with the R-wave supplied from the electrodes 18a, 18b. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A and 2B) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1, 2A and 2B), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

The sample-and-hold circuit 57 is reset whenever the comparator 61 output goes from ONE to ZERO, which occurs when the difference between the baseline mean $O_2$ level in mixed venous blood and current mean $O_2$ level in mixed venous blood returns to an acceptable noncompromising level. The resetting is accomplished by an inverter 77 and a differentiating circuit constituted by a capacitor 78 and a resistor 80 connected in series in the denominated order from the output terminal of the inverter 77 to ground, a positive going spike appearing across the resistor 80 each time the input to the inverter 77 from the comparator 61 goes from ONE to ZERO.

In the event the first pulse delivered to the heart fails to effect a correction in the $O_2$ level in mixed venous blood (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 8, cardioverting/defibrillating D.C. pulses are delivered to the malfunctioning heart only when the rate and the $O_2$ level in mixed venous blood criteria are simultaneously satisfied. This can be viewed as a parallel rate-$O_2$ level algorithm.

In the event the rate criterion is met, but the $O_2$ criteria criteria are not; that is to say no $O_2$ level compromise presents, the circuit of FIG. 8 nevertheless acts to enable an antitachycardia pacemaker 86 which supplies pacing signals to the pair of pacing electrodes 21, 22 (FIGS. 1, 2A and 2B). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no $O_2$ level compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

Figure 9B:
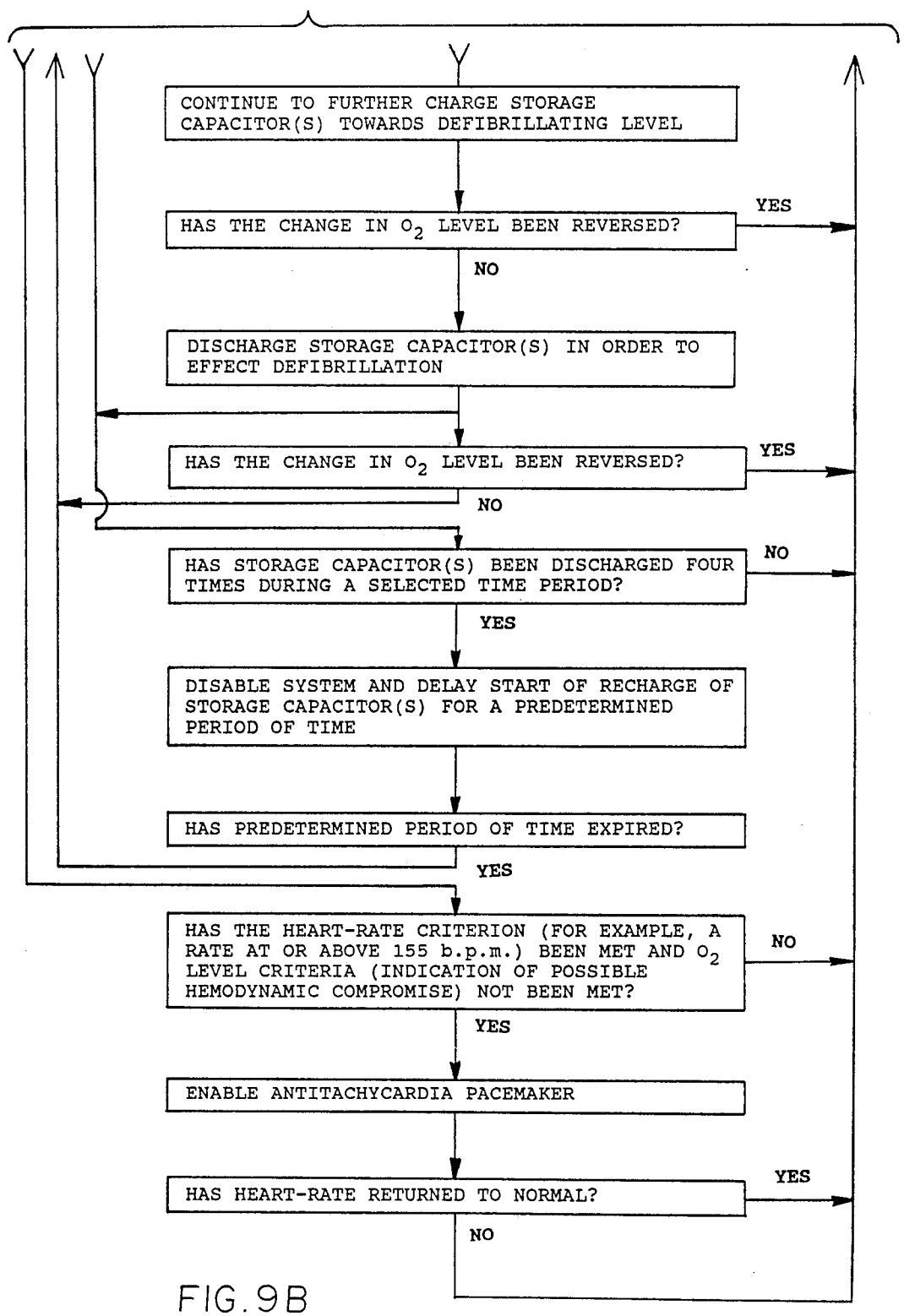

It is to be appreciated that the circuit described above may be considered, at least in part, to be a controller processor, which could be realized as a microprocessor. The processor, with its associated components, in effect carries out the steps set out in the flowchart of FIGS. 9A and 9B.

The circuit of FIG. 8 could be associated with a failsafe antibradycardia pacemaker, if desired.

Figure 11:
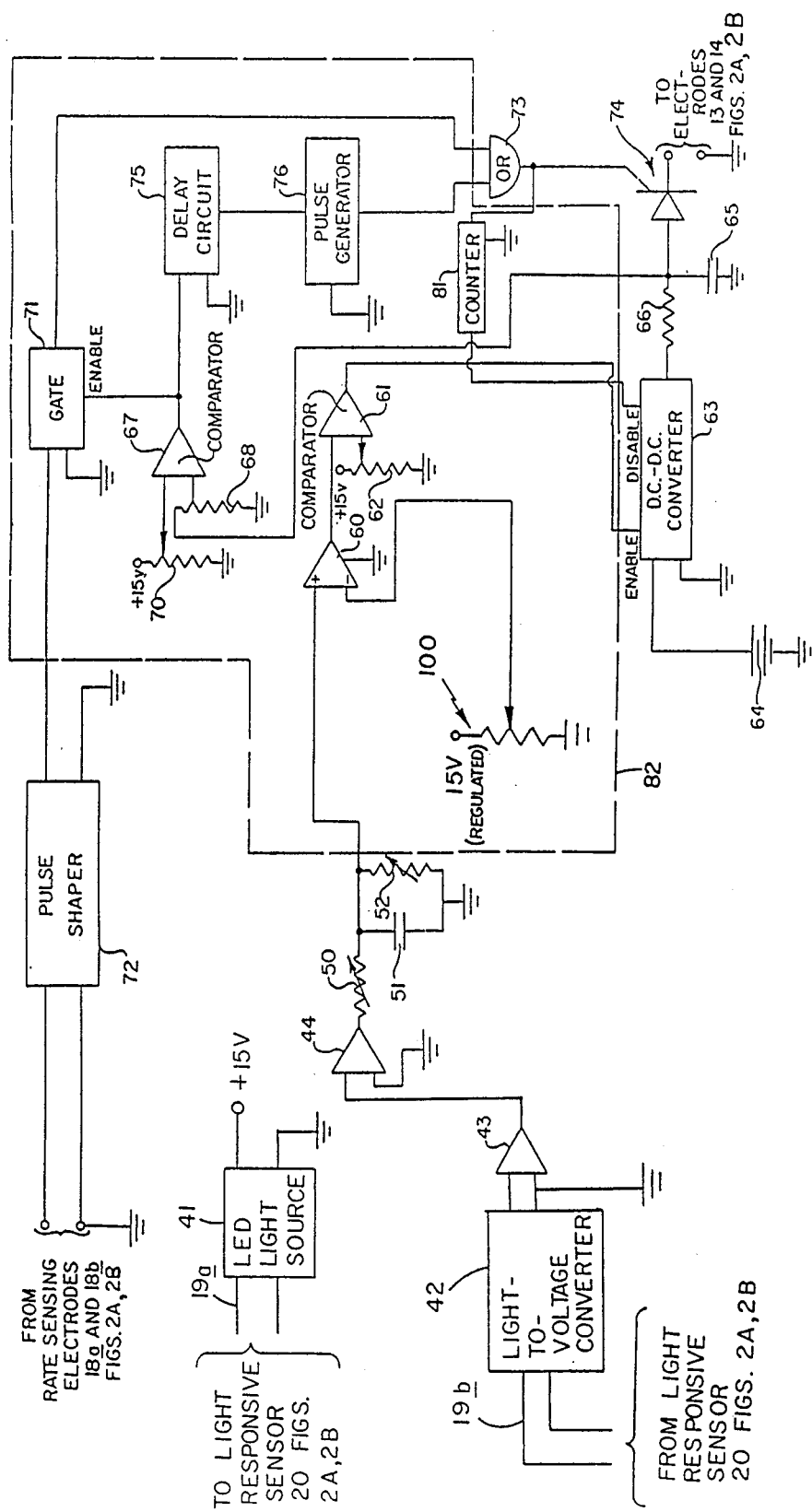
FIG. 11 is a partially block, schematic diagram of a $O_2$ responsive system for treating a malfunctioning heart in accordance with another exemplary embodiment of the invention which is responsive to $O_2$ level in mixed venous blood.

Turning to FIG. 11, an exemplary embodiment of circuit components of the present invention, which may be positioned within the housing 12 (FIGS. 1 and 3), includes a LED light source 41 which produces red light (including the three frequencies mentioned above), the light being carried by the fiberoptic bundle 19a to the sensor 20 (FIGS. 2A, 2B). The light after reflection from red blood corpuscles in mixed venous blood is returned, via the fiberoptic bundle 19b to the light-to-voltage converter 42. The converter 42 produces a varying D.C. voltage output which corresponds to the $O_2$ level of the mixed venous blood. The variable D.C. voltage output signal from the converter 42 represents $O_2$ level of mixed venous blood as sensed by the sensor 20 (FIGS. 1, 2A and 2B). The varying D.C. output voltage from the converter 42 is fed to an amplifier 43, which amplifies the $O_2$ level representing D.C. input signal and feeds the same to a buffer amplifier 44. The circuit of FIG. 11 is suitable for practicing the present invention using a $O_2$ level-only criteria.

A D.C. voltage level (first signal) representative of fixed baseline $O_2$ level for mixed venous blood appears on the wiper of a potentiometer 100 which may be set by a medical professional to suit the particular patient involved. The potentiometer 100 is connected, as illustrated, between system ground and a point of +15 volts, regulated. The medical professional, based on a patient's condition and history, could set the wiper of the potentiometer at a suitable patient-specific point, reflecting an appropriate baseline. It is to be understood that the point may be selected prior to implantation. The circuit may be adapted to enable the patient-specific set point to be changed, the set using radio and/or magnetic coupling (not shown).

The term "mean" as used herein is broad and includes the average value as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean $O_2$ level sensed by the sensor 20 (FIGS. 1, 2A and 2B) over a relatively short period, for example, during the preceding fifteen (15) seconds or longer (for example 60 seconds) or shorter (for example six seconds). The resistors 50 and 52 may be set by a medical professional to suit the particular patient involved, so far as what the most suitable period length (period of given length) for current data acquisition appears to be most suitable. Were the device already implanted, conventional radio or magnetic links could be used to change the setting of the variable resistors 50 and 51 were a patient's condition to make such adjustments desirable.

As illustrated the baseline and short term (current) D.C. voltage signals which appear respectively on the wiper of the potentiometer 100 and across the capacitor 51 are fed respectively to the inverting and noninverting terminals of an operational amplifier 60, a difference D.C. voltage signal appearing as the output from the operational amplifier 60. The D.C. output signal from the operational amplifier 60 is fed to a first input terminal of a first comparator 61, the second input terminal of the comparator 61 is connected to the wiper of a potentiometer 62 which is connected between ground and a point of fixed D.C. potential, illustrated as being +15 volts, from an internal power supply bus.

Whenever the voltage supplied to the comparator 61 from the operational amplifier 60 exceeds the voltage supplied from the potentiometer 62, an indication of $O_2$ level compromise of a patient, the output terminal of the comparator 61 goes from low (ZERO) to high (ONE) which signal is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or a capacitor pack), via a resistor 66 towards the high voltage. The capacitor 65 is of such size that it will store energy levels sufficient to produce the desired cardioverting/defibrillation pulses. The desired pulse may be a truncated exponential pulse of about 25 Joules delivered approximately 17 seconds from onset of the $O_2$ level compromise. The pulse could, especially when defibrillation is being undertaken after a failed attempt to cardiovert, be delivered somewhat later and with a higher energy level.

Once the capacitor 65 is charged to a sufficiently high D.C. voltage level to provide sufficient energy to effect cardioversion, as determined by a comparator 67, which receives on one input terminal a voltage proportional to the increasing D.C. voltage across the capacitor 65, a highly resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input terminal connected to receive an output from a pulse shaper 72, which receives an input from the rate sensing electrodes 18a, 18b (FIGS. 1, 2A and 2B) and produces a pulse train in synchronism with the R-wave supplied from the electrodes 18a, 18b. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy then stored on the capacitor 65 (or the bank of capacitors) into the malfunctioning heart, via the electrodes 13 and 14 (FIGS. 1, 2A and 2B) in an effort to effect cardioversion, the discharge being in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more and enables a pulse generator 76 causing it to produce an output pulse to initiate defibrillation which is supplied, via the OR circuit 73, to the gate electrode of the SCR 74 causing the SCR to fire. The energy storage capacitor 65 (or the bank of capacitors), which by then has charged to a higher level discharges, via the SCR 74 and the electrodes 13 and 14 (FIGS. 1, 2A and 2B), into the malfunctioning heart in an effort to effect defibrillation, the energy level being higher than would have been the case had the capacitor been discharged three seconds earlier. The delay circuit may be composed of an RC circuit connected to the comparator 67 so that the capacitor thereof charges toward the ONE level slowly; for example the capacitor may take about three (3) seconds or more as indicated above to achieve the ONE level, allowing time to receive one or more synchronizing pulses from the pulse shaper 72, if present.

In the event the first pulse delivered to the heart fails to effect a correction in the $O_2$ level (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. An internal timer within the converter 63 holds the converter OFF for a given period so that the patient will not receive more shocks during this given period. At the end of the period the converter 63 returns to a READY condition and is again able to respond to an ENABLE signal from the comparator 61. The counter 81 resets itself to zero whenever it either reaches its maximum count of four or fails to reach the count of four within the given time period.

In the event cardioversion or defibrillation is successful, the short term mean current $O_2$ level (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the $O_2$ level condition sensed indicates that $O_2$ level compromise is again present. In the event the short term mean current $O_2$ level in mixed venous blood returns to normal before the first cardioverting or defibrillating pulse is delivered, the output of the comparator goes to low (ZERO), removing the enable signal from the converter 63, thus stopping the charging of the capacitor 65.

Figure 12A:
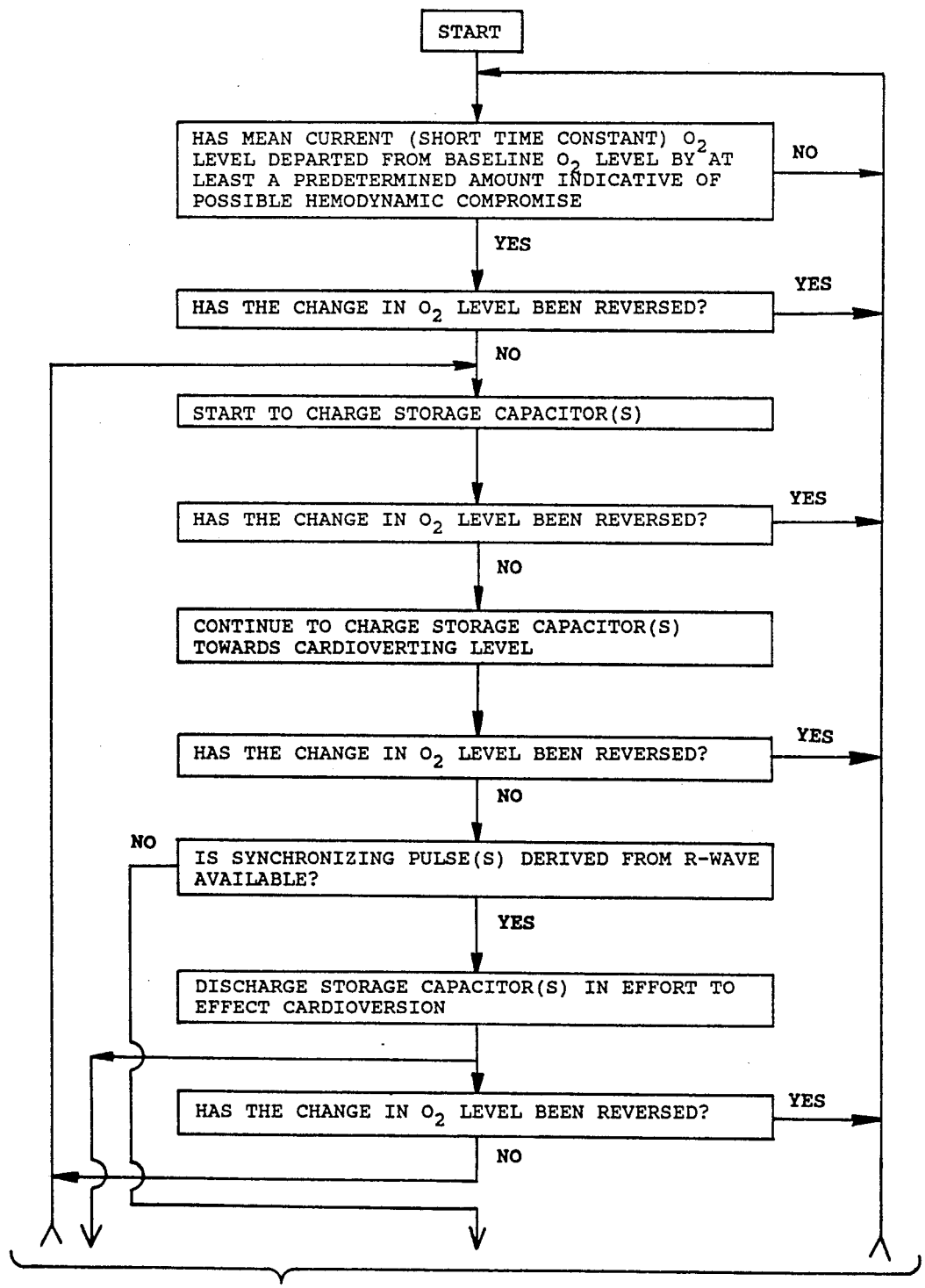
FIGS. 12A and 12B constitute an exemplary flowchart of a series of actions or steps which may be carried out by the system of the present invention illustrated in FIG. 11 and effect achievement of the invention in its method aspect.
Figure 12B:
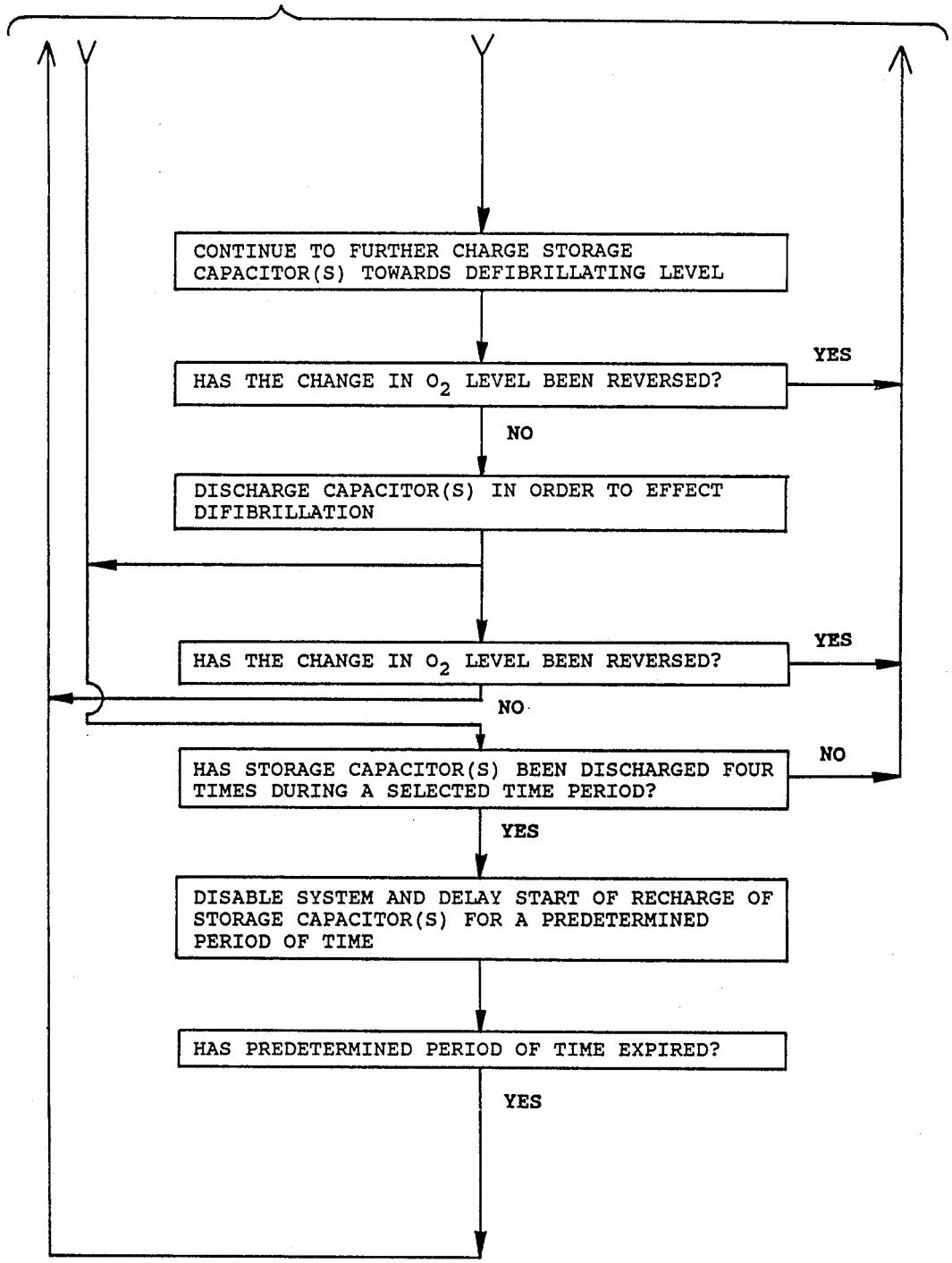

It is to be appreciated that the circuit of FIG. 11 described above may be considered, at least in part, to be a controller or processor, which could be realized as a microprocessor. The processor, with its associated components, in effect carries out the steps set out in the flowchart of FIGS. 12A and 12B.

The circuit of FIG. 11 could be associated with an antitachycardia pacemaker and/or an antibradycardia pacemaker, if desired.

Figure 13:
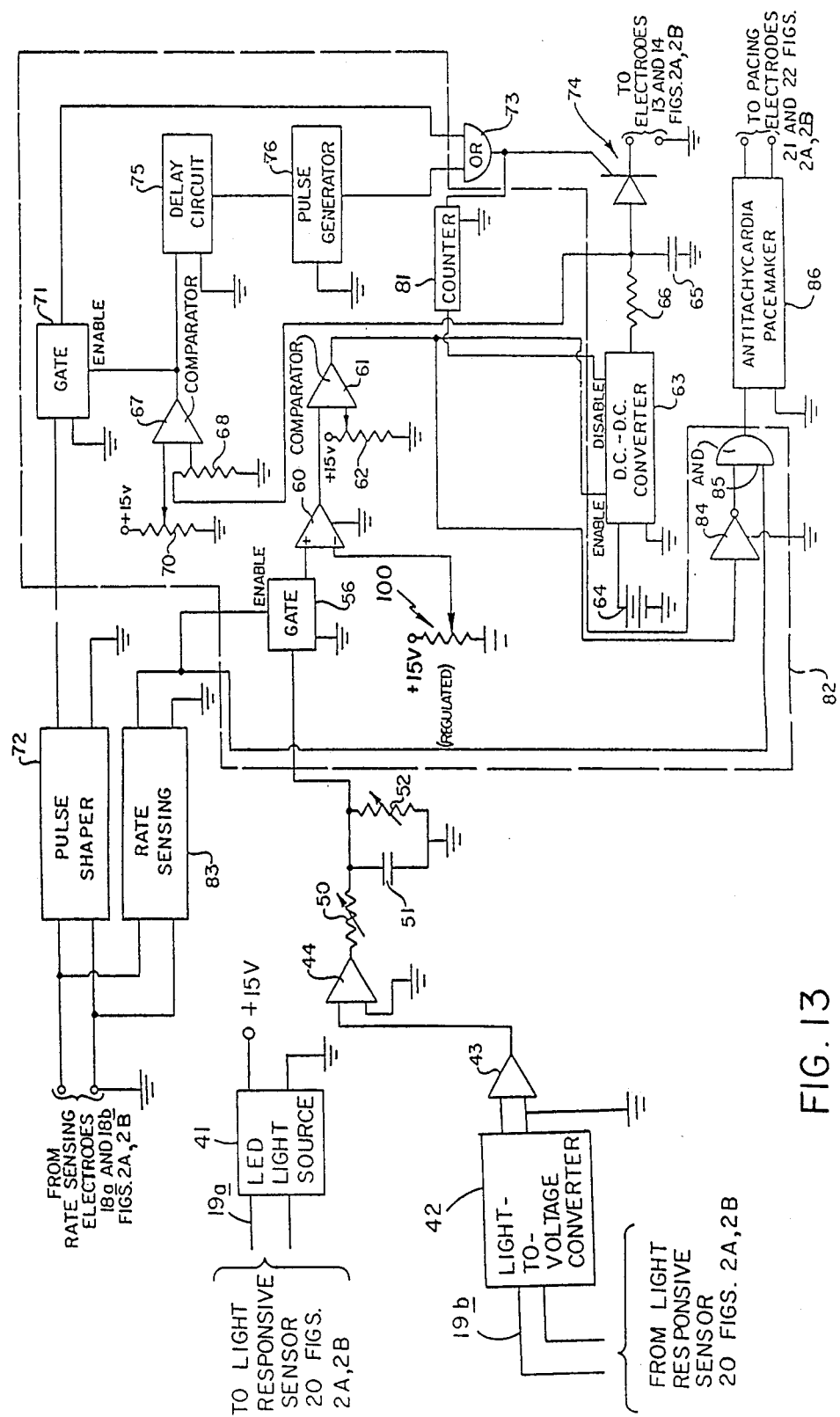
FIG. 13 is a partially block, schematic diagram of an $O_2$ responsive system for treating a malfunctioning heart in accordance with a further exemplary embodiment of the invention which is responsive to $O_2$ level in mixed venous blood and to heart rate.

Turning to FIG. 13, a further exemplary embodiment of the circuit components of the present invention, which may be positioned within the housing 12 (FIGS. 1 and 3) includes a LED light source 41 which produces red light (including the three frequencies mentioned above), the light being carried by the fiberoptic bundle 19a to the sensor 20 (FIGS. 2A, 2B). The light after reflection from red blood corpuscles in mixed venous blood is returned, via the fiberoptic bundle 19b to the light-to-voltage converter 42. The converter 42 produces a varying D.C. voltage output which corresponds to the $O_2$ level of the mixed vneous blood. The variable D.C. voltage output signal from the converter 42 representing $O_2$ level in mixed venous blood from the sensor 20 (FIGS. 1, 2A and 2B) is fed to an amplifier 43, which amplifies the $O_2$ level representing D.C. input signal and feeds the same to a buffer amplifier 44. The circuit of FIG. 13, with associated components, is suitable for practicing the present invention in which both $O_2$ level in mixed venous blood and beating rate criteria are to be taken into account. The rate criterion is examined first and, if met, the $O_2$ level criteria are then considered.

A D.C. voltage level (first signal) provided on the wiper of a potentiometer 100, which is connected between ground and a regulated +15 volts source, represents a fixed baseline $O_2$ level of mixed venous blood. The wiper may be set by a medical professional taking into account the history and condition of the particular patient. The potentiometer 100 may be adjusted, possibly using conventional magnetic or radio links as noted above.

The term "mean" as used herein is broad and includes the average value, as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the capacitor 51 represents the short term mean $O_2$ level sensed by the sensor 20

(FIGS. 1, 2A and 2B) over a relatively short period, for example, during the preceding fifteen (15) seconds or longer (for example 60 seconds) or shorter (for example six seconds). As in the circuit of FIG. 11, the resistors 50 and 51 may be adjusted, taking into account the patient's possibly changing condition, possibly using conventional radio or magnetic links.

As illustrated the baseline and short term (current) D.C. voltage signals appear respective on the wiper of the potentiometer 100 and across the capacitor 51. The voltage (second signal) from the capacitor 51 is fed to the signal input terminal of a gate 56. A rate sensing circuit 83 is arranged to receive a beating rate (R-wave) signal from the rate sensing electrodes 18a, 18b (FIGS. 1, 2A and 2B). Whenever the rate exceeds a given rate, for example 155 beats per minute, indicating tachycardia, the output terminal of the rate sensing circuit 83 goes from low (ZERO) to high (ONE). The ONE signal (first control signal) is supplied as an enabling input to the gate 56. The D.C. voltage representing current mean $O_2$ level in mixed venous blood appearing across the capacitor 51 is fed via the enabled gate 56 to the noninverting input terminal of an operational amplifier 60. The D.C. voltage (first signal) representing baseline $O_2$ level appearing on the wiper of the potentiometer 10 is supplied to the inverting input terminal of the operational amplifier 60 which has its noninverting input terminal connected to the output terminal of the gate 56 which, when enabled as noted above, passes the D.C. voltage signal appearing across the capacitor 51 and representing current mean $O_2$ level in mixed venous blood to the operational amplifier 60.

The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of $O_2$ level compromise, the output terminal of the comparator 61 goes from low (ZERO) to high (ONE) and the signal (second control signal) is passed to the enable terminal of a D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or a pack of capacitors), via a resistor 66 towards the high voltage. The capacitor 65 is of such size that it will store energy levels sufficient to produce the desired cardioverting/defibrillation pulses. The desired pulse for cardioversion may be a truncated exponential pulse of about 25 Joules delivered approximately 17 seconds from onset of the $O_2$ level compromise.

Once the capacitor 65 is charged to a sufficiently high D.C. voltage level to provide sufficient energy to effect cardioversion, as determined by a comparator 67, which receives on one input terminal a voltage proportional to the instant D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A and 2B) and produces a pulse train in synchronism with the R-wave supplied from the electrodes 18a, 18b or from the electrodes 212, 213. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A and 2B) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse to initiate defibrillation. The pulse is supplied, via the OR circuit 73, to the gate electrode of the SCR 74 causing the SCR to fire. The energy storage capacitor 65 (or a pack of capacitors), which during the elapsed three seconds has charged to a higher level, discharges, via the SCR 74 and the electrodes 13 and 14 (FIGS. 1, 2A and 2B), into the malfunctioning heart via the electrodes 13 and 14 (FIGS. 1, 2A and 2B) in an effort to effect defibrillation, the energy level being higher than it would had been had discharge been effected three (3) or more seconds earlier. The delay circuit may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

In the event the first pulse delivered to the heart fails to effect a correction in the $O_2$ level by overcoming the $O_2$ level compromise (which would cause the output of the comparator 61 to become ZERO, removing the enable signal from the converter 63), the capacitor 65 is recharged and discharged a number of additional times, for example three more times in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to ZERO count whenever it either reaches its maximum count of four or fails to reach the count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 13, cardioverting/defibrillating D.C. pulses are delivered to the malfunctioning heart only when the rate criterion is first satisfied and, thereafter, the $O_2$ level criteria also satisfied. This can be viewed as a series rate-$O_2$ algorithm.

In the event the rate criterion is met, but the $O_2$ level criteria are not; that is to say no $O_2$ level compromise presents, the circuit of FIG. 13 nevertheless acts to enable an antitachycardia pacemaker 86 which supplies pacing signals to the pair of pacing electrodes 21, 22 (FIGS. 1, 2A and 2B). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no $O_2$ level compromise prevails, the output terminal of the comparator 61 has a low (ZERO) output. This ZERO output is inverted by the inverter 84 and appears as a ONE on the second input terminal of the AND circuit 85. Thus, when both inputs to the AND circuit 85 are ONE, the antitachycardia pacemaker 86, which may be any one of a number of conventional types is energized.

In the event cardioversion or defibrillation is successful, the short term mean current $O_2$ level (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the $O_2$ level condition sensed indicates that $O_2$ level compromise is again present. In the event the short term current $O_2$ level returns to normal before any cardioverting or defibrillating pulses are delivered (as in the case of FIG. 11), the enable signal is revived from the converter 63 and the charging of the capacitor 65 stops.

Figure 14A:
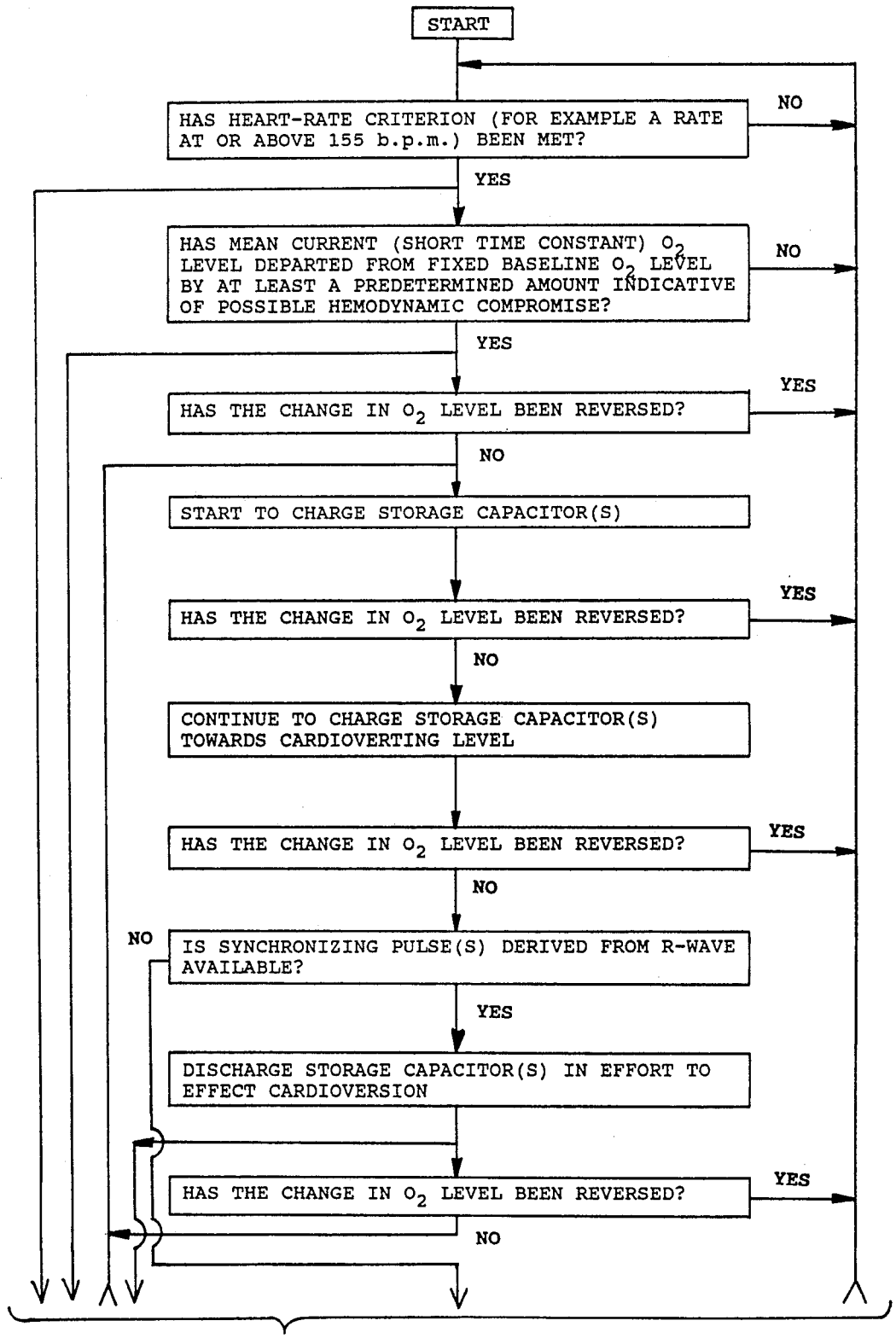
FIGS. 14A and 14B constitute a further exemplary flowchart of a series of actions or steps which may be carried out by the system of the present invention illustrated in FIG. 13 and effect achievement of the invention in its method aspect.
Figure 14B:
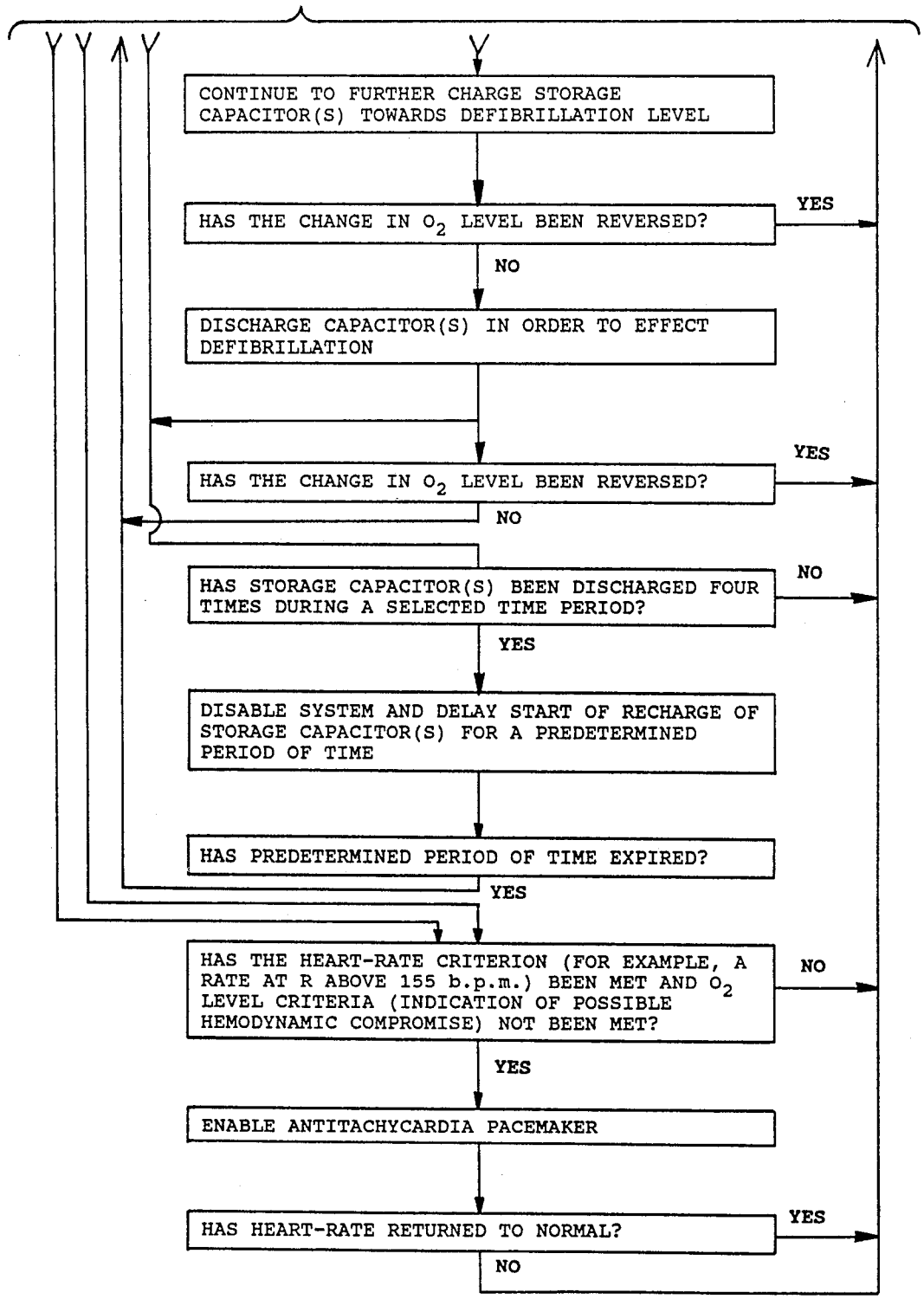

It is to be appreciated that the circuit of FIG. 13 described above may be considered, at least in part, to be a processor, which could be realized as a microprocessor, the processor being identified by the numeral 82. The processor 82, with its associated components, in effect carries out the steps set out in the flowchart of FIGS. 14A and 14B.

It is to be understood that the system of FIG. 13 could be associated with a failsafe antibradycardia pacing system, if desired.

Figure 15:
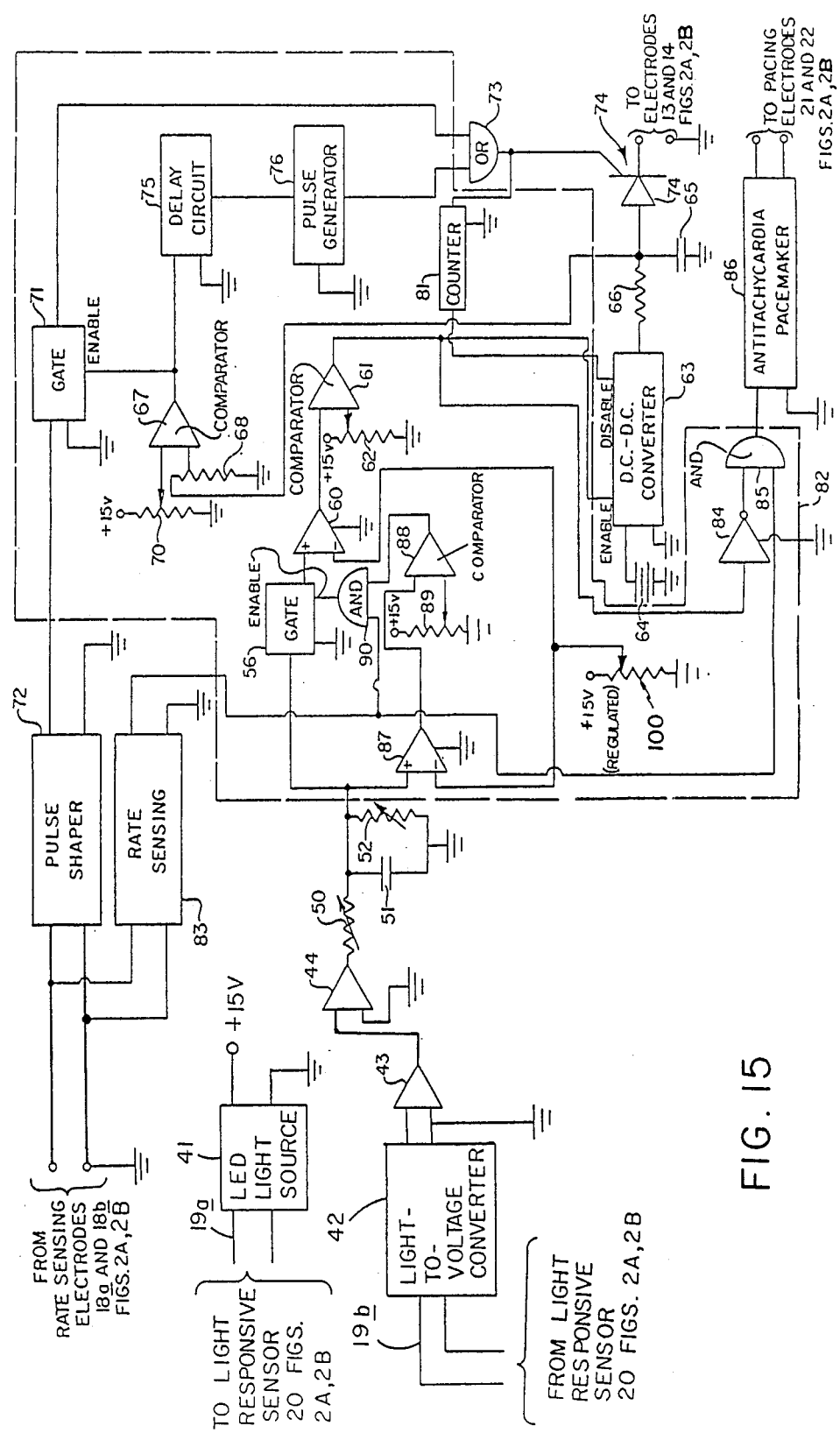
FIG. 15 is a partially block, schematic diagram of O₂ responsive system for treating a malfunctioning heart which is a variant of the circuit of FIG. 13.

Turning to FIG. 15, another exemplary embodiment of the circuit components of the present invention, which may be positioned within the housing 12 (FIGS. 1 and 3) to receive the $O_2$ level representing light from a sensor 20 which receives red light from an LED source 41 via a fiberoptic bundle 19a and return it, via a fiberoptic bundle 19b, to a light-to-voltage converter 42 after reflection from red blood corpuscles. The variable D.C. voltage output signal representing $O_2$ level of mixed venous blood is developed from the light received from the sensor 20 (FIGS. 1, 2A and 2B). The variable D.C. voltage signal is fed to an amplifier 43, which amplifies the $O_2$ level representing D.C. input signal and feeds the same to buffer amplifier 44. The circuit of FIG. 15 can be used in practicing the present invention using both rate and $O_2$ level criteria. In this case the rate and $O_2$ level criteria must exist simultaneously to enable the system.

A D.C. voltage level (first signal) appears on the wiper of a potentiometer 100, which is connected between ground and a regulated +15 volt source, the signal representing fixed baseline $O_2$ level. The wiper (as in the circuits of FIGS. 11 and 13) may be set by a medical professional in accordance with needs of a specific patient and may be adjusted later, if desired, using radio or magnetic techniques.

The term "mean" as used herein is broad and includes the average value, as well as values near the average. The output from the buffer amplifier 44 is supplied to a RC circuit constituted by an adjustable resistor 50 connected to ground via a capacitor 51, which has an adjustable resistor 52 connected in parallel therewith. The time constants (charging and discharging) of these circuit components are such that the D.C. voltage which appears across the capacitor 51 represents the short term mean $O_2$ level sensed by the sensor 20 (FIGS. 1, 2A and 2B) over a relatively short period, for example, during the preceding fifteen (15) seconds or longer (for example 60 seconds) or shorter (for example six seconds). The size of the resistors 50 and 51 (as in the circuits of FIGS. 11 and 13) may be adjusted, a desirable feature were a patient's condition or needs to change.

As illustrated the baseline and short term (current) D.C. voltage signals which respectively appear on the wiper 100 of the potentiometer 100 and across the capacitor 51 are fed respectively to the inverting and noninverting terminals of an operational amplifier 87, a difference D.C. voltage signal appearing as the output from the operational amplifier 87. The D.C. output signal from the operational amplifier 87 is fed to a first input terminal of a comparator 88. The second input terminal of the comparator 88 is connected to the wiper of a potentiometer 89 which is connected between ground and a point of fixed D.C. potential, illustrated as being +15 volts, from an internal power supply bus.

Whenever the voltage supplied to the comparator 88 from the operational amplifier 87 exceeds the voltage supplied via the wiper from the potentiometer 89, a low (ZERO) level on the output terminal from the comparator 88 goes high (ONE), the ONE signal being coupled to a first input terminal of an AND circuit 90 which has its other input terminal coupled to the output terminal of a rate sensing circuit 83, which produces a ONE signal on its output terminal whenever the heart rate exceeds a predetermined value, for example 155 beats per minute. When the AND gate 90 receives ONE signals on both its input terminals, its output goes high (ONE) which enables a gate 56. The voltage (second signal) representing current mean $O_2$ level appearing across the capacitor 51 is fed to the noninverting input terminal of an operational amplifier 60. The voltage (first signal) representing fixed baseline $O_2$ level appearing on the wiper of the potentiometer 100 is fed to the inverting input terminal of the operational amplifier 60. A D.C. output from the sample-and-hold circuit 57 is stored in a storage. The operational amplifier 60 which has its noninverting input terminal connected to the output terminal of the gate 56, which when enabled, passes the D.C. voltage signal appearing across the capacitor 51 and representing current mean $O_2$ level of mixed venous blood to the operational amplifier 60. The output from the operational amplifier 60 is supplied to an input terminal of a comparator 61, which has its other input connected to the wiper of a potentiometer 62 connected between ground and the +15 volt power supply bus. Whenever the voltage supplied to the comparator 61 from the operational amplifier 60 exceeds the voltage supplied from the potentiometer 62, an indication of $O_2$ level compromise of a patient, the output terminal of the comparator 61 goes from low (ZERO) to high (ONE) which signal is passed to the enable terminal of a D.C.-to-D.C. converter 63. It is to be appreciated that the wipers of the potentiometers 89 and 62 can be adjusted independently. Thus, one can set the wiper of the potentiometer 62 so that the $O_2$ level compromise must get worse than it was when the gate 56 was opened before the output from the comparator 61 enables the D.C.-to-D.C. converter 63. The D.C.-to-D.C. converter 63, when enabled, receives current from a low voltage battery pack or battery 64 and converts it into a high D.C. voltage, for example a voltage of 720 volts, which is used, when the converter is enabled, to charge an energy storage capacitor 65 (or capacitor pack), via a resistor 66 towards the high voltage. The capacitor 65 is of such size that it will store energy levels sufficient to produce the desired cardioverting-/defibrillation pulses. The desired pulse for effecting cardioversion may be a truncated exponential pulse of about 25 Joules delivered approximately 17 seconds from onset of the $O_2$ level compromise.

Once the capacitor 65 is charged to a sufficiently high D.C. voltage level, as determined by a comparator 67, which receives on one input terminal a voltage proportional to the D.C. voltage across the capacitor 65, a resistive voltage divider 68 being in parallel to the capacitor 65. The second input terminal of the comparator 67 is connected to the wiper of a potentiometer 70 which is connected between ground and the +15 volt bus. When the voltage across the energy storing capacitor 65 is sufficient to supply a cardioverting energy pulse to the malfunctioning heart, the voltage supplied to the one input terminal of the comparator 67 exceeds the voltage supplied to its other input terminal from the potentiometer 70 via its associated wiper. Under these conditions, the output from the comparator 67 goes from low (ZERO) to high (ONE), which ONE signal effects an enabling of an analog gate 71. The gate 71 has its signal input connected to receive an output from a pulse shaper 72, which receives an input from the rate sensing electrodes 18a, 18b (FIGS. 1, 2A and 2B) and produces a pulse train in synchronism with the R-wave supplied from the electrodes 18a, 18b. If the pulse train from the pulse shaper 72 is present, these pulses are passed, via the gate 71, to an OR circuit 73 and thence to the gate electrode of an SCR 74. The first of these pulses which, if present, appears on the gate electrode fires the SCR 74 thereby discharging the energy stored on the capacitor 65 into the malfunctioning heart, via the electrodes 13 and 14 (FIGS. 1, 2A and 2B) in an effort to effect cardioversion, the discharge being affected in synchronism with the R-wave.

In the event that the pulse shaper 72 does not produce a pulse to fire the SCR 74 because of the absence of an R-wave, the ONE signal from the comparator 67 is passed, via a delay circuit 75, which provides a delay of about three seconds or more, and enables a pulse generator 76 causing it to produce an output pulse which is supplied, via the OR circuit 73, to the gate electrode of the SCR 74 causing the SCR to fire. The energy storage capacitor 65, which by then has been charged to a higher level, discharges, via the SCR 74 and the electrodes 13 and 14 (FIGS. 1, 2A and 2B), into the malfunctioning heart in an effort to effect defibrillation. The delay circuit 75 may be composed of an RC circuit connected to the comparator 67 so that the capacitor thereof charges toward the ONE level slowly; for example the capacitor may take about three (3) seconds or more to achieve the ONE level, allowing time to receive one or more synchronizing pulses from the pulse shaper 72, if present.

In the event the first pulse delivered to the heart fails to effect a correction in the $O_2$ level (which would cause the output of the comparator 61 to become ZERO, removing the enable signal from the converter 63), the capacitor 65 is recharged and discharged a number of additional times, for example three more times, in an effort to correct the malfunction. The number of discharges is sensed by a counter 81, which has its input connected to the output of the OR gate 73. If the counter 81 reaches a count of four within the given time period, for example a period of three minutes, its output goes from ZERO to ONE, which is applied to the converter 63 as a disabling (OFF) signal. The counter 81 resets itself to zero whenever either it reaches its maximum count of four or it fails to reach a count of four within the given time period. An internal timer within the converter 63 holds the converter OFF for a given period so that the patient will not receive more shocks during this given period. At the end of the period the converter 63 returns to a READY condition and is again able to respond to an ENABLE signal from the comparator 61.

As can be seen from the foregoing description of the operation of the circuit of FIG. 15, cardioverting/defibrillating D.C. pulses are delivered to the malfunctioning heart only when the rate and the $O_2$ level criteria are simultaneously satisfied. This can be viewed as a parallel rate-$O_2$ level algorithm.

In the event the rate criterion is met, but the $O_2$ level criteria are not; that is, to say no $O_2$ level compromise presents, the circuit of FIG. 15 nevertheless acts to enable an antitachycardia pacemaker 86 which supplies pacing signals to the pair of pacing electrodes 21, 22 (FIGS. 1, 2A and 2B). To enable the pacemaker 86, two signals must be supplied to an AND circuit 85, the first being a ONE signal from the rate sensing circuit 83, the second being a ONE signal supplied to the AND circuit 85 via an inverter 84 from the output terminal of the comparator 61. When no $O_2$ level compromise prevails, the output terminal of the comparator 61 has a low (ZERO) output. This ZERO output is inverted by the inverter 84 and appears as a ONE on the second input terminal of the AND circuit 85. Thus, when both inputs are ONE, the antitachycardia pacemaker 86 is energized.

In the event cardioversion or defibrillation is successful, the short term mean current $O_2$ level (as reflected by the voltage across the capacitor 51) returns to normal, the output terminal of the comparator 61 goes low (ZERO) from high (ONE) thereby removing the enabling input from the converter 63 and stopping the charging of the capacitor 65. The system is thus made ready for another sequence in the event the $O_2$ level condition sensed indicates that $O_2$ level compromise is again present.

Figure 16A:
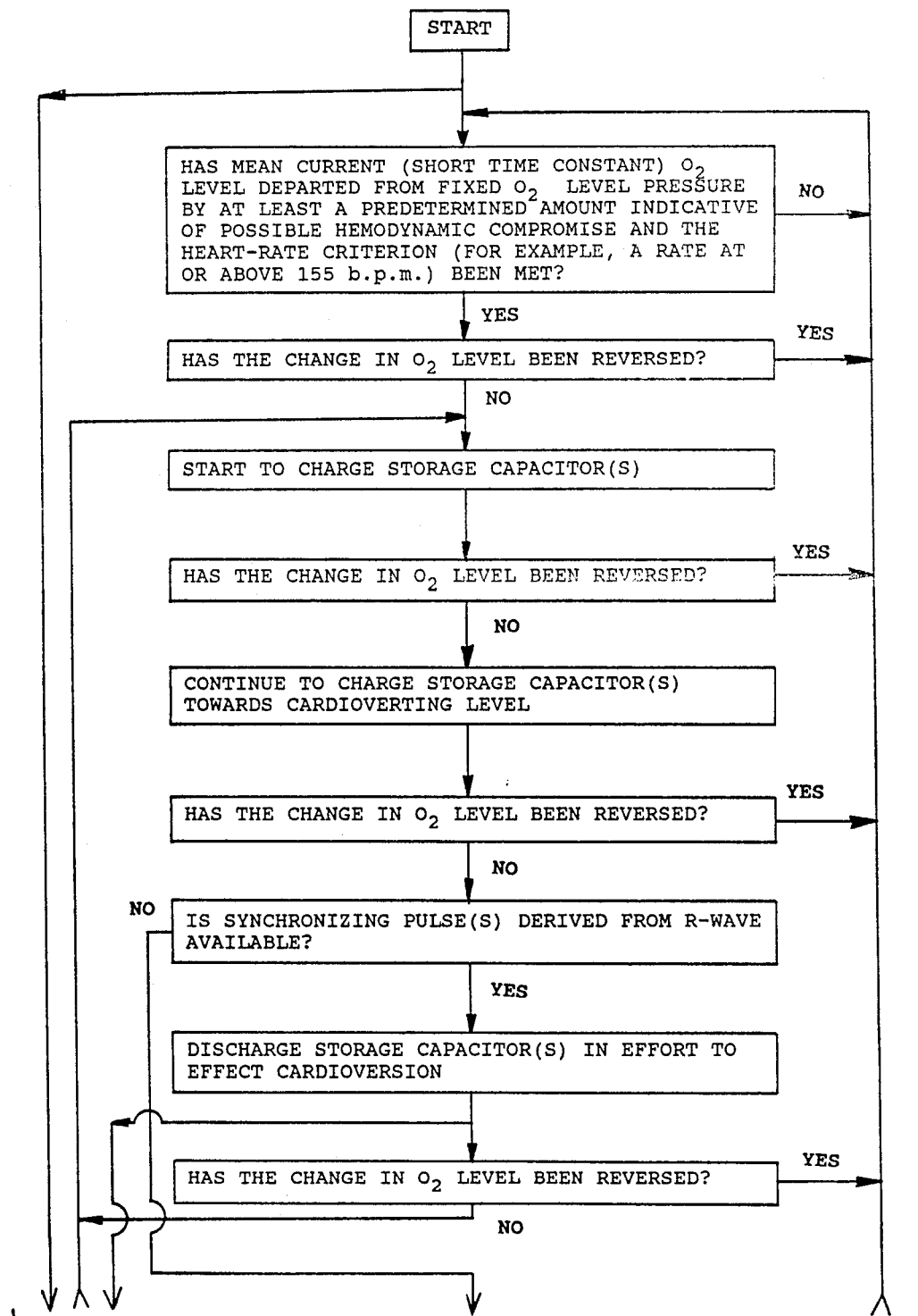
FIGS. 16A and 16B constitute an additional exemplary flowchart of a series of actions or steps which may be carried out by the system of the present invention as illustrated in FIG. 15 and effect achievement of the invention in its method aspect.
Figure 16B:
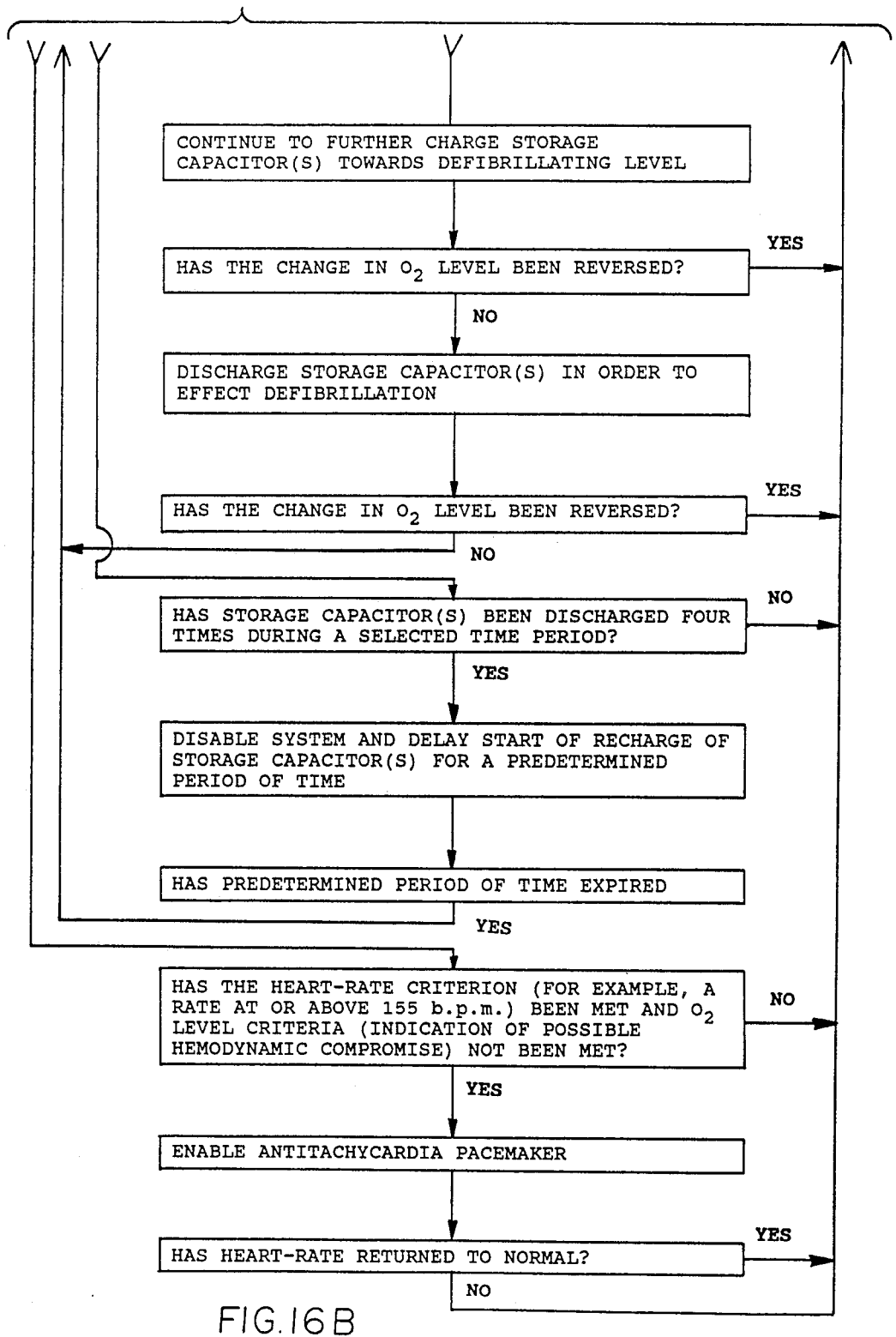

It is to be appreciated that the circuit of FIG. 15 described above may be considered, at least in part, to be a controller processor, which could be realized as a microprocessor, the processor being identified by the numeral 82. The processor 82, with its associated components, in effect carries out the steps set out in the flowchart of FIGS. 16A and 16B.

The circuit of FIG. 15 could be associated with a failsafe antibradycardia pacemaker, if desired.

Figure 10:
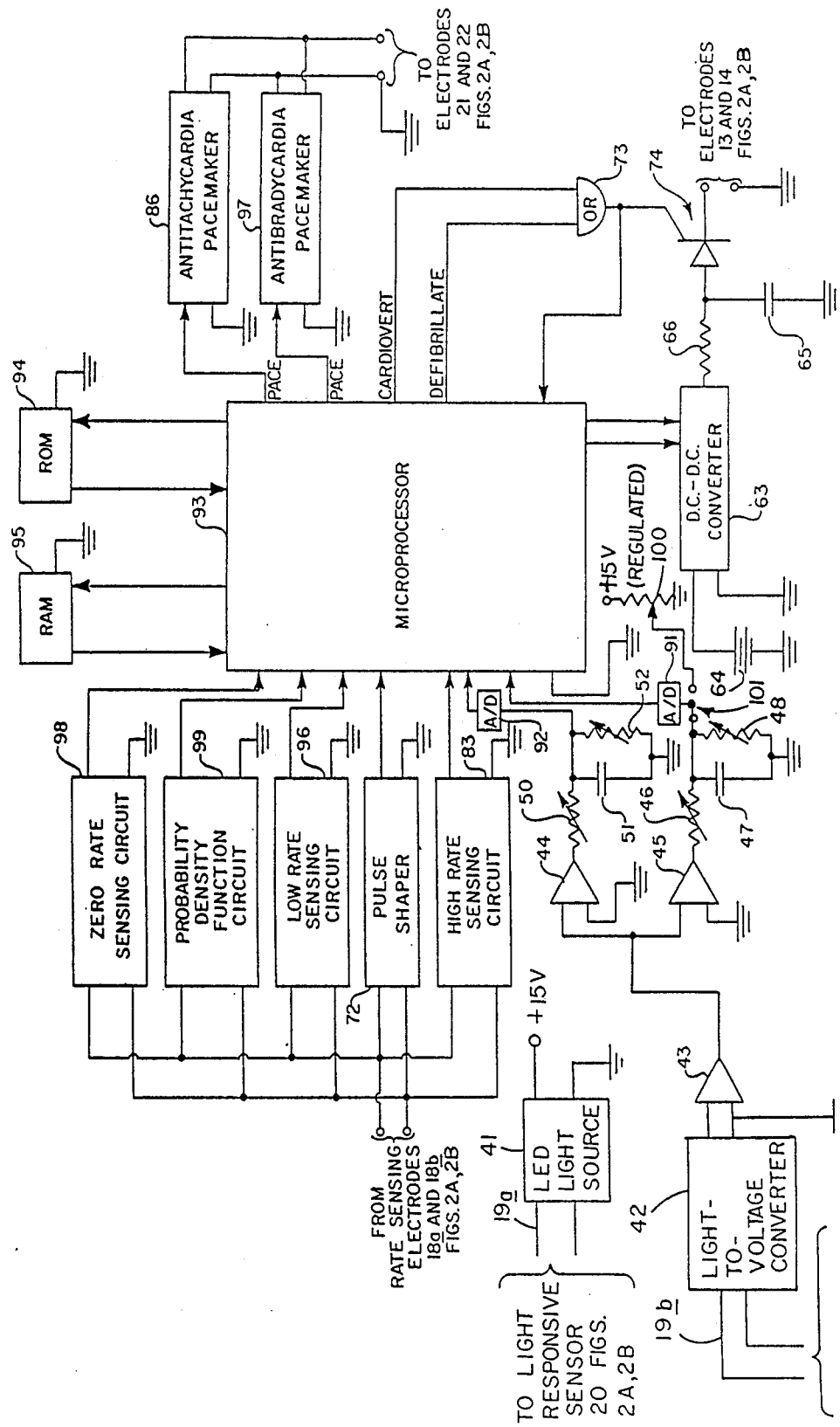
FIG. 10 is a partially block, schematic diagram of a $O_2$ responsive system for treating a malfunctioning heart which provides a microprocessor implementation in accordance with preferred embodiments of the present invention, as well as those illustrated in FIGS. 4, 6 and 8.

Turning to FIG. 10, an exemplary embodiment of circuit components of a system for treating a malfunctioning heart, which may be positioned within the housing 12 (FIGS. 1 and 3) or used in a portable system which may be carried on the body of a patient or used in fixed installation, such as in ICU's, CCU's, hospital rooms and the like includes a LED light source 41 which produces red light (including the three frequencies mentioned above), the light being carried by the fiberoptic bundle 19a to the sensor 20 (FIGS. 2A, 2B). The light after reflection from red blood corpuscles in mixed venous blood is returned, via the fiberoptic bundle 19b to the light-to-voltage counter 42. The converter 42 produces a varying D.C. voltage output which corresponds to the $O_2$ level of the mixed venous blood. The variable D.C. voltage output signal representing $O_2$ level in mixed venous blood from is developed by a light-to-voltage connector 42. The D.C. voltage output signal is fed to an amplifier 43, which amplifies the $O_2$ level representing D.C. input signal and feeds the same to respective buffer amplifiers 44 and 45. The circuit of FIG. 10 can be used in practicing the present invention using either $O_2$ level criterion alone or both rate and $O_2$ level criteria (either in parallel or series). The circuit of FIG. 10 can be used to carry out the methods, illustrated as algorithms in the flowcharts of FIGS. 5A, 5B and 7A, 7B and 9A, 9B, 12A, 12B and 14A, 14B and 16A, 16B. The circuit of FIG. 10 can be considered as a digital, microprocessor-based version of the hand-wired analogue circuitry shown in FIGS. 4, 6 and 8, when the single-pole, double-throw switch 101 is set as shown. In the other position of the switch 101, the circuit can be considered to be a digital, microprocessor-based version of the hand-wired analogue circuitry illustrated in FIGS. 11, 13 and 15. Of course, the microprocessor-based circuit of FIG. 10 could be programmed to carry out other routines. For example, were a rate criterion to be satisfied, the circuit could be arranged (1) simply to monitor $O_2$ level of mixed venous blood, (2) to effect antitachycardia pacing and/or to cardiovert. As further examples, were both rate and $O_2$ level criteria to be satisfied, the circuit of FIG. 10 could be programmed (1) to effect antitachycardia pacing and/or (2) to cardiovert/defibrillate. Moreover, the selected interventions could be programmed so that when one is tried and fails, another is tried and so on. For example, if a tachycardia were detected regardless of whether or not $O_2$ level compromise is present an antitachycardia pacemaker would attempt early to revert the arrhythms to normal and if this fails cardioversion/defibrillation would then attempt the same. A detailed discussion of one possible program is discussed below.

The output from the buffer amplifier 45 is supplied to an RC circuit constituted by an adjustable resistor 46 connected to ground via a series connected storage capacitor 47 having a large adjustable resistor 48 connected in parallel therewith. The time constants (charging and discharging) of these circuit components are such that the D.C. voltage (first signal) across the capacitor 47 represents the mean $O_2$ level of mixed venous blood sensed by the sensor 20 (FIGS. 1, 2A and 2B) over a relatively long period, for example during the preceding fifteen (15) minutes or even longer (for example a number of hours) of shorter (for example 120 seconds) being suitable in some cases. The D.C. voltage level across the capacitor 47 thus represents a long term mean baseline $O_2$ level. The term "mean" as used herein is broad and includes the average value as well as values near the average. The output from the buffer amplifier 44 is supplied to a second RC circuit constituted by an adjustable resistor 50 connected to ground via a capacitor 51, which has an adjustable resistor 52 connected in parallel therewith. The time constants (charging and discharging) of these circuit components are such that the D.C. voltage (second signal) which appears across the resistor 51 represents the short term mean $O_2$ level in mixed venous blood sensed by the sensor 20 (FIGS. 1, 2A and 2B) over a relatively short period, for example, during the preceding fifteen (15) seconds or longer (for example 60 seconds) or shorter (for example six seconds).

As illustrated the long term (baseline) and short term (current) D.C. voltage signals which appear across the respective capacitors 47 and 51 are fed respectively via respective analogue-to-digital converters (A/D's) 91 and 92 to respective inputs of a microprocessor 93. The A/D converters 91 and 92, in operation, convert the respective analogue signals which appear across capacitors 47 and 51 into corresponding digital signals for processing by the microprocessor 93, the microprocessor having associated therewith a ROM 94, which supplies programmed instructions to the microprocessor, and a RAM 95, which stores and supplies digital signal representations of $O_2$ level-related signals from and to the microprocessor.

Another input of the microprocessor 93 is supplied with high (ONE) and low (ZERO) signals from a high rate sensing circuit 83, which produces a ONE signal whenever the heart rate, as sensed by the electrodes 18a and 18b (FIGS. 2A and 2B), exceeds a predetermined rate, for example a rate of 155 b.p.m. The actual rate selected would, of course, depend on the individual patient and a professional opinion as to his or her condition. A pulse shaper 72, which also receives an input from the rate sensing electrodes 18a and 18b (FIGS. 2A and 2B), is provided to supply narrow D.C. pulses to the microprocessor 93; if present, these pulses would be used as synchronizing pulses for cardioversion.

An antitachycardia pacemaker 86 is connected to an output terminal of the microprocessor 93 to receive therefrom a pace enable signal to, in effect, enable or turn on the pacemaker 86 under the command of the microprocessor 93. Two other output terminals from the microprocessor 93 provide respective cardiovert and defibrillate command signals to an OR circuit 73, which cooperates with a D.C.-to-D.C. converter 63, a battery 64, a charging resistor 66, storage capacitor 65 and a SCR 74 in the same manner as the corresponding circuit components having the same reference numerals function in the hand-wired circuits illustrated in FIGS. 4, 6 and 8. The output of the OR gate 73 is also supplied to an input terminal of the microprocessor 93, supplying signals to a counting means within the microprocessor 93 which corresponds to the counter 81 (FIGS. 4, 6 and 8).

As thus far described, the circuit of FIG. 10 can carry out the methods defined in the flowcharts of FIGS. 5A, 5B and 7A, 7B and 9A, 9B, the respective programs being supplied by the ROM 94. In operation, the circuit of FIG. 10, with the switch 101 set as illustrated, can be seen as a microprocessor realization of the hand-wired analogue circuits of FIGS. 4, 6 and 8. With the switch 101 set in its other position, the capacitor 47 and the resistor 48 are disconnected from the input to the A/D converter 91 and the wiper of the potentiometer 100 connected thereto. The voltage which appears on the wiper of the potentiometer 100 thus constitutes the first signal, representing in this case the fixed baseline $O_2$ level. The circuit of FIG. 10 when so connected to a carry out the methods defined in the flowcharts of FIGS. 12A, 12B and 14A, 14B and 16A, 16B. It is to be appreciated that the circuit of FIG. 10 can be programmed to effect somewhat different routines and be provided with additional inputs, as well.

If desired for example, a low rate sensing circuit 96 could be provided, its input being coupled to the rate sensing electrodes 18a and 18b (FIGS. 2A and 2B). The low rate sensing circuit 96 supplies a high (ONE) signal to an input terminal whenever the beating rate, as sensed by the electrodes 18a and 18b or the electrodes 212 and 213, falls below a given rate, for example 45 b.p.m., indicative of bradycardia. Under these conditions (provided the rate were not zero), the microprocessor 93 would provide a command enable signal to an antibradycardia pacemaker 97. When enabled, the pacemaker 97 would supply bradycardia-correcting pacing signals to a patient's heart via the pacing electrodes 21 and 22 (FIGS. 1, 2A and 2B).

If desired, a zero rate sensing circuit 98, responsive to output from the rate sensing electrodes 18a and 18b (FIGS. 2A and 2B) can be provided. This zero rate sensing circuit 98 produces a high (ONE) output signal whenever the beating rate is zero, indicating the heart has stopped beating (sometimes referred to as going "flat line"). This may represent either asystole or fine ventricular fibrillation. Under this condition, the microprocessor 93 is programmed to first effect a charging and discharging of the storage capacitor 65, supplying a ONE signal via its command defibrillate output connection to the OR gate 73 and then to effect antibrachycardia pacemaking after a given number of capacitor(s) discharges (say 4) if no hemodynamic improvement is noted. The order of defibrillation and pacemaking may be programmed in a reverse manner as desired.

The circuit of FIG. 10 includes, if desired, a narrow window probability density function circuit 99, which has its input coupled to the sensing electrodes 18a and 18b or sensing electrodes 212 and 213. The probability density function circuit may be of the type disclosed in U.S. Pat. Nos. 4,184,493, 4,202,340 and 4,475,551 of Langer et al. and which produce a high (ONE) output signal whenever fine ventricular fibrillation is present. This ONE output is supplied to an input of the microprocessor 93 which, in accordance with its program stored in the ROM 94, effects the charging and discharging of the storage capacitor 65, supplying via its command defibrillate output a ONE signal to the OR gate 73 to initiate discharge.

Conventional antitachycardia systems function primarily as rate-only sensing devices and perform inadequately in differentiating hemodynamically stable from unstable tachycardias. Consequently, in the course of developing the present invention, the $O_2$ level in mixed venous blood was studied by applicant for determining if a basis was present to distinguish significant arrhythmias and serve as a criteria for improving antitachycardia systems.

The present invention provides significant advancements in the treatment of patients having malfunctioning hearts. The systems of the present invention operate automatically. The baseline $O_2$ level and permitted deviations therefrom are not based on an average of a large sampled population or standard; rather, these parameters are patient-specific.

It is to be understood that the foregoing detailed description and accompanying illustrations have been set out by way of example, not by way of limitation. Numerous other embodiments and variants are possible, without departing from the spirit and scope of the invention, its scope being defined in the appended claims.

What is claimed is:

1. A cardioverting/defibrillating system for treating a malfunctioning heart of a patient, the system comprising, in combination, storage means for storing electrical energy, electrode means for electrically coupling the storage means to the heart, sensing means for sensing $O_2$ level in blood within a site in a circulatory system, means for providing a first signal representative of baseline $O_2$ level, means responsive to output from the sensing means for developing a second signal representing current $O_2$ level in blood at the site over a period of given duration, and means responsive to output from the means for providing the first signal and output from the means for developing the second signal for charging and enabling discharge of the electrical energy stored by the storage means across the electrode means to effect cardioversion/defibrillation upon change indicative of patient-compromise in the current $O_2$ level in blood at the site of at least a predetermined magnitude from the representative baseline $O_2$ level in blood.

2. The system according to claim 1, wherein the means providing a signal representative baseline $O_2$ level is constituted by means providing a signal representative of fixed baseline $O_2$ level in blood.

3. The system according to claim 2, wherein said sensing means is constituted by means for sensing $O_2$ level of mixed venous blood.

4. The system according to claim 2, wherein said sensing means is constituted by means for sensing $O_2$ level in mixed venous blood within a right ventricle of a heart.

5. The system according to claim 2, wherein said sensing means is constituted by means for sensing $O_2$ level in mixed venous blood within a pulmonary artery.

6. The system according to claim 1, wherein the means for providing a first signal representative of baseline $O_2$ level is constituted by means for developing a variable first signal representative of mean baseline $O_2$ level in blood at the site over a period of predetermined duration which is greater than the period of given duration.

7. The system according to claim 6, wherein said sensing means is constituted by means for sensing $O_2$ level of mixed venous blood.

8. The system according to claim 6, wherein said sensing means is constituted by means for sensing $O_2$ level in mixed venous blood within a right ventricle of a heart.

9. The system according to claim 6, wherein said sensing means is constituted by means for sensing $O_2$ level in mixed venous blood within a pulmonary artery.

10. The system according to claim 1, including means responsive to the first signal and to the second signal for providing a control signal indicative of the current $O_2$ level differing by at least a predetermined amount from the baseline $O_2$ level, and the means for charging and enabling discharge is responsive to the control signal.

11. The system according to claim 1, including a microprocessor for developing a control signal to control the means for charging and enabling discharge of the electrical energy stored by the storage means.

12. The system according to claim 1, including means for sensing heart rate to produce a distinctive control signal upon the heart rate exceeding a predetermined rate; controllable antitachycardia pacemaking means for supplying pacing signals to the heart; controllable cardioverting/defibrillating means, including the storage means for storing electrical energy; control circuit means, responsive to the distinctive control signal and to an output from the means for charging and enabling discharge, for enabling the antitachycardia pacemaking means in response to presence of the distinctive control signal and contemporaneous absence of the output from the means for charging and enabling, and for enabling the cardioverting/defibrillating means in response to contemporaneous presence of both the distinctive control signal and the output from the means for charging and enabling.

13. The system according to claim 12, including means responsive to output from said means for sensing heart rate for developing a discharge-synchronizing signal synchronized to an R-wave, and the means for discharging electrical energy across the electrode means and into the heart includes means for synchronizing the discharge with the discharge-synchronizing signal to effect cardioversion.

14. The system according to claim 13, wherein the means for discharging electrical energy across the electrode means and into the heart effects discharge on a nonsynchronized basis, in the absence of the synchronization signal, to effect defibrillation.

15. The system according to claim 1, including means for discharging electrical energy across said electrode means and into the heart effects discharge on a nonsynchronized basis to effect defibrillation.

16. The system according to claim 1, further including antitachycardia pacemaking means for supplying tachycardia-correcting signals to the heart.

17. A cardioverting/defibrillating method of treating a malfunctioning heart comprising sensing $O_2$ level in blood at a site of a circulatory system, providing a representation of baseline $O_2$ level, determining current $O_2$ level in blood at the site from the sensed level at the site over a period of given duration, and delivering cardioverting/defibrillating electrical energy to the heart in response to change of at least a predetermined magnitude indicative of patient-compromise in the current $O_2$ level in blood at the site from the baseline $O_2$ level.

18. The method according to claim 17, wherein the step of providing a representation of baseline $O_2$ level in blood comprises providing a fixed representation of baseline $O_2$ level in blood at the site.

19. The method according to claim 18, wherein the step of sensing $O_2$ level in blood at the site is constituted by sensing $O_2$ level in mixed venous blood at the site.

20. The method according to claim 19, wherein the step of sensing $O_2$ level in mixed venous blood at the site is constituted by sensing $O_2$ level in mixed venous blood within a right ventricle of a heart.

21. The method according to claim 19, wherein the step of sensing $O_2$ level in mixed venous blood at the site is constituted by sensing $O_2$ level in mixed venous blood within a pulmonary artery.

22. The method according to claim 17, wherein the step of providing a representative of baseline $O_2$ level in blood at the site comprises providing a varying representation of mean baseline $O_2$ level in blood at the site over a period of predetermined duration which is greater than the period of given duration.

23. The method according to claim 22, wherein the step of sensing $O_2$ level in blood at the site is constituted by sensing $O_2$ level in mixed venous blood at the site.

24. The method according to claim 23, wherein the step of sensing $O_2$ level in mixed venous blood at the site is constituted by sensing $O_2$ level in mixed venous blood within a right ventricle of a heart.

25. The method according to claim 23, wherein the step of sensing $O_2$ level in mixed venous blood at the site is constituted by sensing $O_2$ level in mixed venous blood within a pulmonary artery.

26. The method according to claim 17, wherein the step of delivering cardioverting/defibrillating electrical energy is taken upon current $O_2$ level in blood at the site differing from baseline $O_2$ level in blood at the site by at least the predetermined magnitude.

27. The method according to claim 17, including sensing heart rate, the step of delivering cardioverting/defibrillating electrical energy being taken upon heart rate exceeding a given rate and the current $O_2$ level in blood at the site differing from baseline $O_2$ level in blood at the site by at least a predetermined magnitude.

28. The method according to claim 17, further including supplying tachycardia-correcting signals to the heart in absence of patient-compromise and the presence of tachycardia.

29. A cardioverting/defibrillating system for treating a malfunctioning heart comprising, in combination, storage means for storing electrical energy, electrode means for electrically coupling the storage means to the heart, sensing means for sensing $O_2$ level in blood at a site in a circulatory system, means for providing a first signal representative of baseline $O_2$ level in blood at the site, means for developing a second signal representing current $O_2$ level in blood at the site, and means responsive to output from the means for providing the first signal and output from the means for developing the second signal for charging and enabling discharge of the electrical energy stored by the storage means across the electrode means to effect cardioversion/defibrillation upon change indicative of patient compromise in the current $O_2$ level at the site of at least a predetermined magnitude from the representative baseline $O_2$ level in blood at the site.

30. The system according to claim 29, further including means for supplying tachycardia-correcting signals to the heart in absence of patient-compromise and presence of tachycardia.

31. A cardioverting/defibrillating method of treating a malfunctioning heart comprising sensing $O_2$ level in blood within a site in a circulatory system, providing a representation of baseline $O_2$ level in blood at the site, determining current $O_2$ level in blood at the site from the sensed level, and discharging electrical energy into the heart to effect cardioversion/defibrillation in response to change of at least a predetermined magnitude in the current $O_2$ level in blood at the site from the baseline $O_2$ level in blood at the site indicative of patient-compromise.

32. The method according to claim 31, further including supplying tachycardia-correcting signals to the heart in absence of patient-compromise and presence of tachycardia.

33. A cardioverting/defibrillating system for treating a malfunctioning heart comprising sensing means for sensing $O_2$ level in blood within a site in a circulatory system, means for providing a first signal representative of baseline O₂ level in blood at the site, means responsive to output from the sensing means for developing a second signal representing current O₂ level in blood at the site, and means responsive to output from the means for providing the first signal and output from the means for developing the second signal for enabling electrical means to effect cardioversion/defibrillation of the malfunctioning hear upon change indicative of patient-compromise in the current O₂ level in blood at the site of at least a predetermined magnitude from the representative baseline O₂ level in blood at the site.

34. The system according to claim 33, wherein the means providing a signal representative baseline O₂ level in blood at the site is constituted by means providing a signal representative of fixed baseline O₂ level in blood at the site.

35. The system according to claim 34, wherein said sensing means is constituted by sensing means for sensing O₂ level in mixed venous blood.

36. The system according to claim 35, wherein said sensing means is constituted by sensing means for sensing O₂ level in mixed venous blood within a right ventricle of a heart.

37. The system according to claim 35, wherein said sensing means is constituted by means for sensing O₂ level in mixed venous blood within a pulmonary artery.

38. The system according to claim 33, wherein the means for providing a first signal representative of baseline O₂ level is constituted by means for developing a variable first signal representative of mean baseline O₂ level in blood at the site over a period of predetermined duration.

39. The system according to claim 38, wherein said sensing means is constituted by sensing means for sensing O₂ level in mixed venous blood.

40. The system according to claim 39, wherein said sensing means is constituted by sensing means for sensing O₂ level in mixed venous blood within a right ventricle of a heart.

41. The system according to claim 39, wherein said sensing means is constituted by means for sensing O₂ level in mixed venous blood within a pulmonary artery.

42. The system according to claim 33, further including means for supplying tachycardia-correcting signals to the heart in absence of patient-compromise and presence of tachycardia.

43. A cardioversion/defibrillation system for treating a malfunctioning heart comprising means for monitoring O₂ in blood at a site within a circulator system of a patient to provide an output representing O₂ level in blood at the site and means responsive to the output for supplying cardioverting/defibrillating energy to the heart upon the O₂ level in blood at the site falling to or below a patient-compromising level.

44. The system according to claim 43, including means for supplying tachycardia-correcting signals to the heart.

45. A cardioverting/defibrillating method of treating a malfunctioning heart comprising continuously monitoring O₂ level in blood at at a site in a patient's circulatory system, and delivering cardioverting/defibrillating energy to the malfunctioning heart upon the O₂ level in blood at the site falling to or below a patient-compromising level.

46. The method according to claim 45, further including supplying Tachycardia-correcting signals to the heart in absence of patient-compromise and presence of tachycardia.

47. In a system for treating a malfunctioning heart of the type which includes storage means for storing electrical energy, electrode means for electrically coupling the storage means to the heart, sensing means for sensing O₂ level in mixed venous blood within a pulmonary artery in a circulatory system, means for providing a first signal representative of fixed baseline O₂ level, means responsive to output from the sensing means for developing a second signal representing current O₂ level in blood at the site over a period of given duration, and means responsive to output from the means for providing the first signal and output from the means for developing the second signal for charging and enabling discharge of the electrical energy stored by the storage means across the electrode means upon change in the current O₂ level in blood within said pulmonary artery of at least a predetermined amount from the representative baseline O₂ level in blood.

48. The system according to claim 47, including means responsive to the first signal and to the second signal for providing a control signal indicative of the current O₂ level differing by at least a predetermined amount from the baseline O₂ level, and the means for charging and enabling discharge is responsive to the control signal.

49. The system according to claim 47, including a microprocessor for developing a control signal to control the means for charging and enabling discharge of the electrical energy stored by the storage means.

50. The system according to claim 47, including means for sensing heart rate to produce a distinctive control signal upon the hear rate exceeding a predetermined rate; controllable antitachycardia pacemaking means for supplying pacing signals to the heart; controllable cardioverting/defibrillating means, including the storage means for storing electrical energy; control circuit means, responsive to the distinctive control signal and to an output from the means for charging and enabling discharge, for enabling the antitachycardia pacemaking means in response to presence of the distinctive control signal and contemporaneous absence of the output from the means for charging and enabling, and for enabling the cardioverting/defibrillating means in response to contemporaneous presence of both the distinctive control signal and the output from the means for charging and enabling.

51. The system according to claim 50, including means responsive to output from said means for sensing heart rate for developing a discharge-synchronizing signal synchronized to an R-wave, and the means for discharging electrical energy across the electrode means and into the heart includes means for synchronizing the discharge with the discharge-synchronizing signal to effect cardioversion.

52. The system according to claim 51, wherein the means for discharging electrical energy across the electrode means and into the heart effects discharge on a nonsynchronized basis, in the absence of the synchronization signal, to effect defibrillation.

53. The system according to claim 47, including means for discharging electrical energy across said electrode means and into the heart effects discharge on a nonsynchronized basis to effect defibrillation.

54. In a system for treating a malfunctioning heart of the type which includes storage means for storing electrical energy, electrode means for electrically coupling the storage means to the heart, sensing means for sensing O₂ level in mixed venous blood within a pulmonary artery in a circulatory system, means for providing a variable first signal representative of a variable baseline $O_2$ level, means responsive to output from the sensing means for developing a second signal representing current $O_2$ level in blood at the site over a period of given duration, and means responsive to output from the means for providing the first signal and output from the means for developing the second signal for charging and enabling discharge of the electrical energy stored by the storage means across the electrode means upon change in the current $O_2$ level in blood within said pulmonary artery of at least a predetermined amount from the representative baseline $O_2$ level in blood.

55. The system according to claim 54, including means responsive to the first signal and to the second signal for providing a control signal indicative of the current $O_2$ level differing by at least a predetermined amount from the baseline $O_2$ level, and the means for charging and enabling discharge is responsive to the control signal.

56. The system according to claim 54, including a microprocessor for developing a control signal to control the means for charging and enabling discharge of the electrical energy stored by the storage means.

57. The system according to claim 54, including means for sensing heart rate to produce a distinctive control signal upon the heart rate exceeding a predetermined rate; controllable antitachycardia pacemaking means for supplying pacing signals to the heart; controllable cardioverting/defibrillating means, including the storage means for storing electrical energy; control circuit means, responsive to the distinctive control signal and to an output from the means for charging and enabling discharge, for enabling the antitachycardia pacemaking means in response to presence of the distinctive control signal and contemporaneous absence of the output from the means for charging and enabling, and for enabling the cardioverting/defibrillating means in response to contemporaneous presence of both the distinctive control signal and the output from the means for charging and enabling.

58. The system according to claim 57, including means responsive to output from said means for sensing heart rate for developing a discharge-synchronizing signal synchronized to an R-wave, and the means for discharging electrical energy across the electrode means and into the heart includes means for synchronizing the discharge with the discharge-synchronizing signal to effect cardioversion.

59. The system according to claim 58, wherein the means for discharging electrical energy across the electrode means and into the heart effects discharge on a nonsynchronized basis, in the absence of the synchronization signal, to effect defibrillation.

60. The system according to claim 54, including means for discharging electrical energy across said electrode means and into the heart effects discharge on a nonsynchronized basis to effect defibrillation.

61. A method of treating a malfunctioning heart comprising sensing $O_2$ level in mixed venous blood at within a pulmonary artery of a circulatory system, providing a representation of baseline $O_2$ level, determining current $O_2$ level in blood within said pulmonary artery from the sensed level within said pulmonary artery over a period of given duration, and delivering cardioverting/defibrillating electrical energy to the heart in response to change of at least a predetermined magnitude in the current $O_2$ level in blood within said pulmonary artery from the baseline $O_2$ level.

62. The method according to claim 61, wherein the step of providing a representation of baseline $O_2$ level in blood comprises providing a fixed representation of baseline $O_2$ level in blood within said pulmonary artery.

63. The method according to claim 61, wherein the step of providing a representative of baseline $O_2$ level in blood within said pulmonary artery comprises providing a varying representation of mean baseline $O_2$ level in blood within said pulmonary artery over a period of predetermined duration which is greater than the period of given duration.

64. The method according to claim 61, including sensing heart rate, the step of delivering cardioverting-/defibrillating electrical energy being taken upon the heart rate exceeding a given rate and the current $O_2$ level in blood at the site differing from baseline $O_2$ level in blood at the site by at least a predetermined magnitude.

65. A system for treating a malfunctioning heart comprising sensing means for sensing $O_2$ level in mixed venous blood within a pulmonary artery in a circulatory system, means for providing a first signal representative of baseline $O_2$ level in blood at said pulmonary artery, means responsive to output from the sensing means for developing a second signal representing current $O_2$ level in blood within said pulmonary artery, and means responsive to output from the means for providing the first signal and output from the means for developing the second signal for enabling electrical means for correcting the malfunction upon change in the current $O_2$ level in blood within said pulmonary artery of at least a predetermined amount from the representative baseline $O_2$ level in blood within said pulmonary artery.

66. The system according to claim 65, wherein the means providing a signal representative baseline $O_2$ level in blood within said pulmonary artery is constituted by means providing a signal representative of fixed baseline $O_2$ level in blood at the site.

67. The system according to claim 65, wherein the means for providing a first signal representative of baseline $O_2$ level is constituted by means for developing a variable first signal representative of mean baseline $O_2$ level in blood within said pulmonary artery over a period of predetermined duration.

* * * * *